(12) United States Patent
Yang et al.

(10) Patent No.: US 12,070,527 B2
(45) Date of Patent: Aug. 27, 2024

(54) UV SANITIZING APPARATUS

(71) Applicant: FKA Distributing Co., LLC, Commerce Township, MI (US)

(72) Inventors: David Yang, Coquitlam (CA); Deepa Mani, South Lyon, MI (US); Thomas Galloway, Commerce Township, MI (US)

(73) Assignee: FKA Distributing Co., LLC, Commerce Township, MI (US)

( * ) Notice: Subject to any disclaimer, the term of this patent is extended or adjusted under 35 U.S.C. 154(b) by 0 days.

(21) Appl. No.: 18/366,045

(22) Filed: Aug. 7, 2023

(65) Prior Publication Data

US 2023/0372568 A1 Nov. 23, 2023

Related U.S. Application Data

(62) Division of application No. 16/912,701, filed on Jun. 25, 2020, now Pat. No. 11,779,671.

(Continued)

(51) Int. Cl.
*A61L 2/26* (2006.01)
*A61L 2/10* (2006.01)

(52) U.S. Cl.
CPC ........ *A61L 2/26* (2013.01); *A61L 2/10* (2013.01); *A61L 2202/11* (2013.01);
(Continued)

(58) Field of Classification Search
CPC .... A61L 2/10; A61L 2202/14; A61L 2202/11; A61L 9/20; A61L 2202/16;
(Continued)

(56) References Cited

U.S. PATENT DOCUMENTS

| D306,784 S | 3/1990 | Fung |
|---|---|---|
| D466,259 S | 11/2002 | Wang |

(Continued)

FOREIGN PATENT DOCUMENTS

| CN | 102596262 A | 7/2012 |
|---|---|---|
| CN | 105307722 A | 2/2016 |

(Continued)

OTHER PUBLICATIONS

International Search Report and Written Opinion for Application No. PCT/US2020/039710, dated Oct. 15, 2020, 11 pages.

(Continued)

*Primary Examiner* — David A Vanore
(74) *Attorney, Agent, or Firm* — Brooks Kushman P.C.

(57) ABSTRACT

A portable sanitizing apparatus, such as a case, includes a first case portion arranged to receive an object to be sanitized, and a second case portion connected to the first case portion and including at least one UV light source configured to emit UV electromagnetic radiation. The second case portion includes an expansion member having a collapsed configuration and an expanded configuration. When the expansion member is in the expanded configuration, a distance between the second case portion and the first case portion is increased compared to when the expansion member is in the collapsed configuration, thereby increasing a distance from the at least one UV light source to the object to be sanitized.

21 Claims, 16 Drawing Sheets

Related U.S. Application Data

(60) Provisional application No. 62/866,226, filed on Jun. 25, 2019.

(52) U.S. Cl.
CPC ..... *A61L 2202/122* (2013.01); *A61L 2202/14* (2013.01); *A61L 2202/16* (2013.01)

(58) Field of Classification Search
CPC .. A61L 2209/111; A61L 2/26; A61L 2209/12; A61L 2/0047; A61L 2/08; A61N 2005/0644; A61N 2005/0661; A61N 5/0624; A61N 5/0616; A61N 2005/0652; A61N 2005/0654
See application file for complete search history.

(56) References Cited

U.S. PATENT DOCUMENTS

| | | | |
|---|---|---|---|
| 7,084,389 B2* | 8/2006 | Spector | A61N 5/0616 250/227.13 |
| D579,164 S | 10/2008 | Cheng | |
| D661,812 S | 6/2012 | Griffin et al. | |
| 8,399,853 B2 | 3/2013 | Roiniotis | |
| D679,825 S | 4/2013 | Elkerbout et al. | |
| 8,481,970 B2 | 7/2013 | Cooper et al. | |
| 8,662,705 B2* | 3/2014 | Roberts | A61L 2/10 362/249.02 |
| D717,298 S | 11/2014 | Sale et al. | |
| 8,964,405 B2 | 2/2015 | La Porte et al. | |
| D739,987 S | 9/2015 | Bushaw | |
| 9,339,570 B2 | 5/2016 | Whitney | |
| 9,339,576 B2 | 5/2016 | LaPorte et al. | |
| D759,922 S | 6/2016 | Valley | |
| D775,445 S | 12/2016 | Cole | |
| D779,140 S | 2/2017 | Lim et al. | |
| D795,515 S | 8/2017 | Cole | |
| D803,410 S | 11/2017 | Im et al. | |
| 9,839,707 B2* | 12/2017 | Won | A61L 2/10 |
| 9,855,351 B2 | 1/2018 | Kim | |
| D810,952 S | 2/2018 | Hsu | |
| 9,925,390 B2 | 3/2018 | Yehezkel | |
| 10,265,540 B2 | 4/2019 | Yehezkel | |
| 10,279,059 B2* | 5/2019 | Bettles | A61L 2/10 |
| D864,485 S | 10/2019 | Ouyang et al. | |
| 10,500,294 B2 | 12/2019 | Paul et al. | |
| 10,610,609 B2 | 4/2020 | Swaney et al. | |
| D883,511 S | 5/2020 | Li | |
| D903,125 S | 11/2020 | Burns et al. | |
| D904,981 S | 12/2020 | Worthy | |
| D907,316 S * | 1/2021 | Stewart | D32/35 |
| 10,969,262 B1* | 4/2021 | Zhang | G01F 23/268 |
| 11,007,292 B1* | 5/2021 | Grenon | A61L 2/24 |
| D936,579 S * | 11/2021 | Wang | D24/217 |
| 11,185,605 B2* | 11/2021 | Jin | A61L 2/24 |
| 11,364,318 B2* | 6/2022 | Yang | B65D 21/086 |
| 11,452,793 B1* | 9/2022 | Fulbrook | A61L 9/205 |
| 2004/0256581 A1* | 12/2004 | Au | A61L 2/10 250/504 H |
| 2005/0145801 A1 | 7/2005 | Huang et al. | |
| 2006/0079948 A1* | 4/2006 | Dawson | A61N 5/0624 607/94 |
| 2008/0260601 A1* | 10/2008 | Lyon | B01D 53/007 422/186.3 |
| 2010/0104471 A1* | 4/2010 | Harmon | A61L 2/10 422/186.3 |
| 2011/0104017 A1* | 5/2011 | Migliore | C02F 1/002 422/186.3 |
| 2011/0243789 A1* | 10/2011 | Roberts | A61L 2/10 422/116 |
| 2012/0313006 A1* | 12/2012 | Chiu | A61L 2/10 250/455.11 |
| 2013/0063922 A1* | 3/2013 | La Porte | A61L 2/10 250/455.11 |
| 2013/0243647 A1* | 9/2013 | Garner | A61L 2/24 250/492.1 |
| 2014/0001374 A1* | 1/2014 | Ullman | A61L 9/205 250/492.1 |
| 2014/0127077 A1* | 5/2014 | Rock | A61L 2/10 604/20 |
| 2015/0068942 A1 | 3/2015 | Gerstner et al. | |
| 2015/0190538 A1* | 7/2015 | Olvera | A61L 2/24 250/455.11 |
| 2015/0287561 A1* | 10/2015 | Levesque | H01H 36/00 190/100 |
| 2016/0000950 A1* | 1/2016 | Won | A61L 2/10 250/455.11 |
| 2016/0088868 A1* | 3/2016 | Dobrinsky | A23L 3/28 250/492.1 |
| 2016/0106873 A1* | 4/2016 | Dobrinsky | G01N 21/6456 250/393 |
| 2017/0173363 A1* | 6/2017 | Wang | A61N 5/1048 |
| 2017/0216466 A1* | 8/2017 | Dujowich | A61L 2/0047 |
| 2018/0093005 A1* | 4/2018 | Nakamoto | A61L 9/122 |
| 2018/0104367 A1* | 4/2018 | Bettles | A61L 2/10 |
| 2018/0117192 A1 | 5/2018 | Baranov et al. | |
| 2018/0117194 A1* | 5/2018 | Dobrinsky | G01N 21/6486 |
| 2018/0308327 A1* | 10/2018 | Dobbins | G08B 13/1427 |
| 2018/0326105 A1* | 11/2018 | Crosby | A61L 2/10 |
| 2018/0343847 A1* | 12/2018 | Ervin | A61L 2/10 |
| 2018/0357385 A1* | 12/2018 | LaPorte | A61L 2/08 |
| 2019/0184044 A1* | 6/2019 | Yellen | A61L 2/10 |
| 2019/0224352 A1* | 7/2019 | Rasooly | A61L 2/10 |
| 2020/0093945 A1* | 3/2020 | Jeong | A61N 5/0625 |
| 2020/0215214 A1* | 7/2020 | Rosen | A61L 2/084 |
| 2020/0390917 A1* | 12/2020 | Tang | A61L 2/10 |
| 2021/0145995 A1* | 5/2021 | Majdali | A61L 2/22 |
| 2021/0346541 A1* | 11/2021 | Callahan | A61L 2/10 |
| 2022/0031889 A1* | 2/2022 | Hanna | A61L 2/10 |
| 2022/0296754 A1* | 9/2022 | Strauss | B25J 15/0061 |
| 2022/0387641 A1* | 12/2022 | Daczko | A61L 2/10 |
| 2023/0131699 A1* | 4/2023 | LaPorte | A61L 2/28 250/454.11 |

FOREIGN PATENT DOCUMENTS

| | | |
|---|---|---|
| CN | 108013562 A | 5/2018 |
| CN | 304697001 S | 6/2018 |
| CN | 208165702 U | 11/2018 |
| CN | 209075577 U | 7/2019 |
| CN | 305554531 S | 1/2020 |
| JP | D1644216 | 10/2019 |
| KR | 1020150066443 A | 6/2015 |
| KR | 1020160039070 A | 4/2016 |
| KR | 1020160107036 A | 9/2016 |
| WO | 2015167319 A1 | 11/2015 |
| WO | 2016003967 A1 | 1/2016 |

OTHER PUBLICATIONS

Turner, "Commerce Township's HoMedics to Produce Masks/PPE in Response to COVID-19", https://www.oaklandcountyprosper.com/...merce-township/commerce-townships-homedics-to-produce-masks-ppe-in-response-to-covid-19, Aug. 15, 2020, 3 pages.

https://www.masqd.com/products/portable-uv-lightbox, "Mask & Phone Sanitizing Case—UV Light Powered—MASQD", retrieved Aug. 17, 2020, 7 pages.

Office Action for U.S. Appl. No. 29/696,071, dated Aug. 20, 2020, 5 pages.

International Preliminary Report on Patentability for Application No. PCT/US2020/039710, dated Jan. 6, 2022, 8 pages.

Chinese Decision of Rejection with English translation for Application No. 202080045797.0, dated Feb. 27, 2024, 20 pages.

* cited by examiner

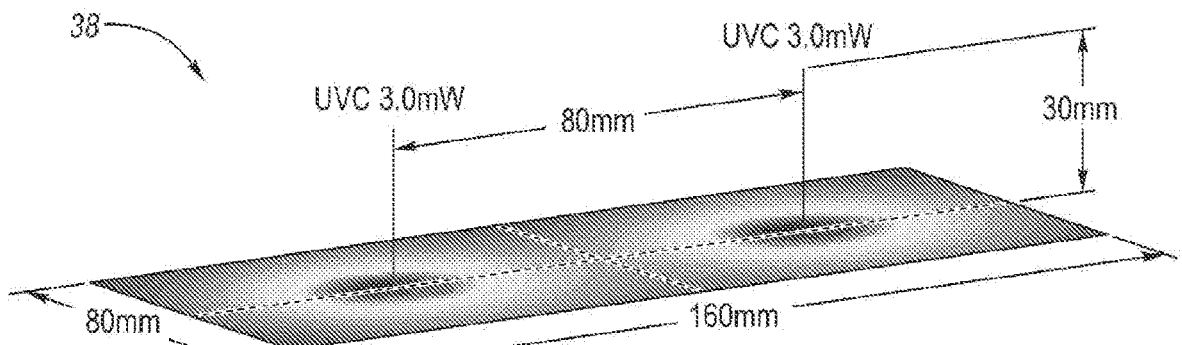
FIG. 10
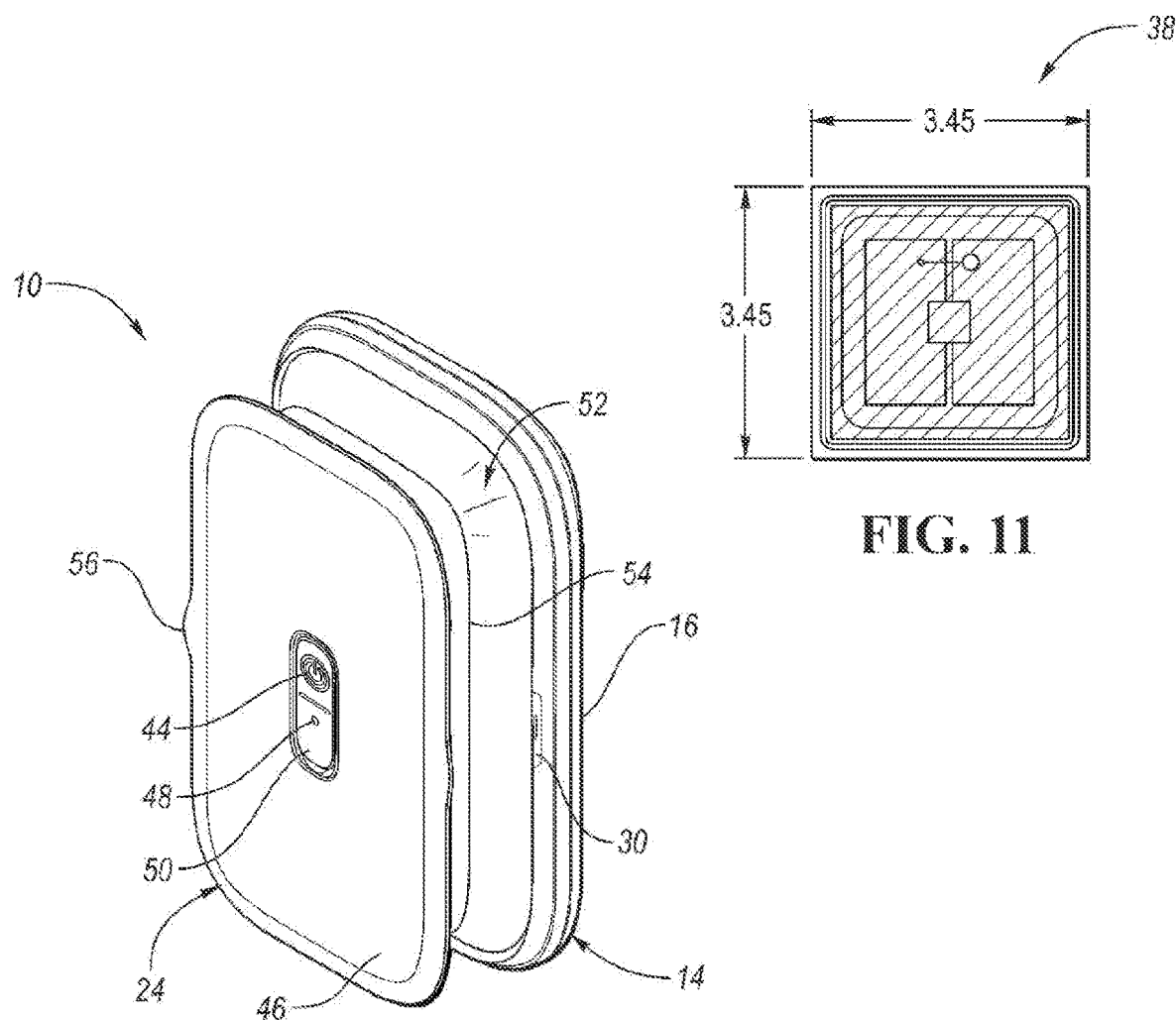
FIG. 11
FIG. 12

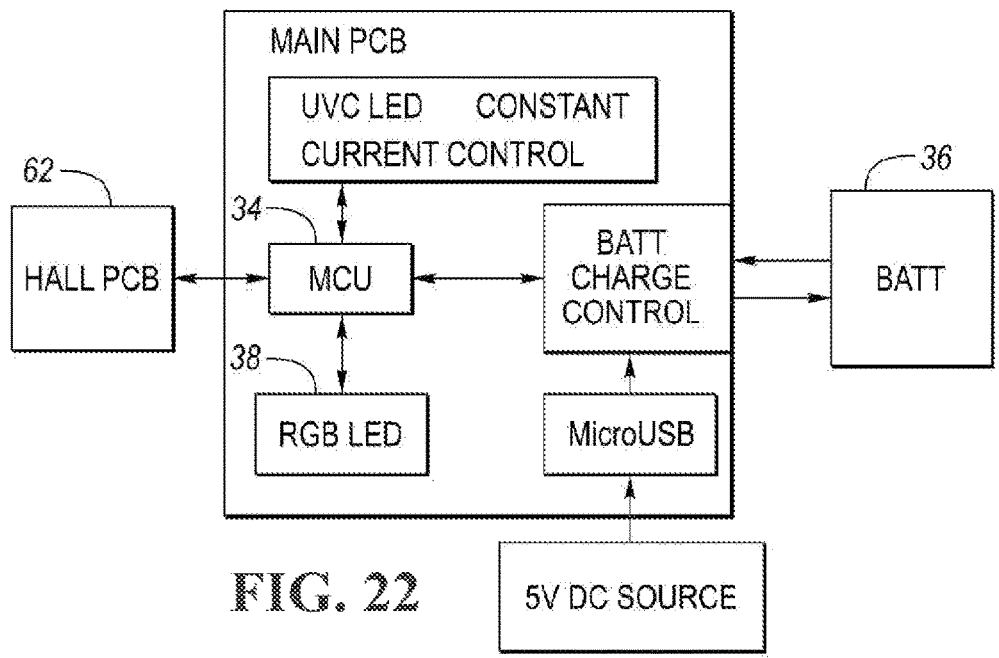
FIG. 22
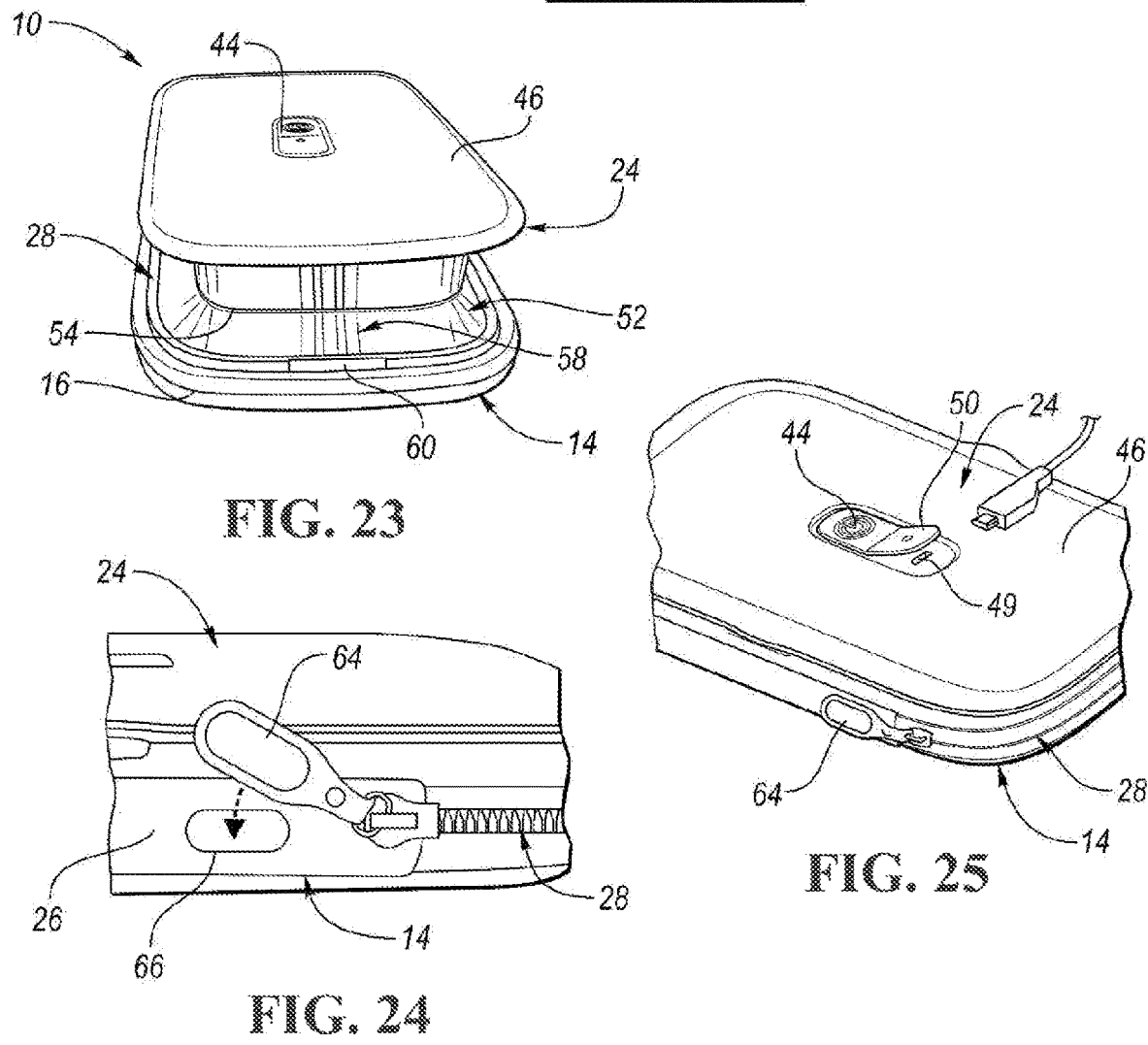
FIG. 23
FIG. 24
FIG. 25

UV SANITIZING APPARATUS

CROSS-REFERENCE TO RELATED APPLICATIONS

This application is a division of U.S. application Ser. No. 16/912,701 filed Jun. 25, 2020, now U.S. Pat. No. 11,779,671, which, in turn, claims the benefit of U.S. provisional application Ser. No. 62/866,226 filed Jun. 25, 2019, the disclosures of which is hereby incorporated in their entirety by reference herein.

TECHNICAL FIELD

Embodiments relate to a portable sanitizing apparatus which uses ultraviolet light to sanitize objects and surfaces.

BACKGROUND

For better or worse, people take their smartphones, tablets, and other electronic devices everywhere. On average, mobile devices such as these may be handled approximately one hundred times per day and are used in the car, the office, the gym, the kitchen, and the bathroom, too. Unsurprisingly, electronic devices easily become contaminated, where cell phones can harbor nearly 20,000 distinct types of bacteria, germs and viruses. In order to prevent the spread of such microorganisms or pathogens, the surfaces of mobile devices should be kept clean. In addition to mobile devices, items such as credit cards, keys, watches, and other small objects which are frequently touched can also benefit from sterilization. While disinfecting liquids or wipes may be used for this purpose, these are often not items that people carry with them at all times, and the chemicals in these products may not be desirable for the consumer.

SUMMARY

In one or more embodiments, a portable sanitizing case includes a first case portion arranged to receive an object to be sanitized, and a second case portion connected to the first case portion and including at least one UV light source configured to emit UV electromagnetic radiation. The second case portion includes an expansion member having a collapsed configuration and an expanded configuration. When the expansion member is in the expanded configuration, a distance between the second case portion and the first case portion is increased compared to when the expansion member is in the collapsed configuration, thereby increasing a distance from the at least one UV light source to the object to be sanitized.

In one or more embodiments, a portable sanitizing wand includes a top housing portion including at least one UV light source configured to emit UV electromagnetic radiation, and a base portion arranged to be placed over a surface or object to be sanitized. An expansion member is connected between the top housing portion and the base portion, the expansion member having a collapsed configuration and an expanded configuration. When the expansion member is in the expanded configuration, a distance between the top housing portion and the base portion is increased compared to when the expansion member is in the collapsed configuration, thereby increasing a distance from the at least one UV light source to the surface or object to be sanitized.

In one or more embodiments, a portable sanitizing case includes a first case portion arranged to receive an object to be sanitized, and a second case portion connected to the first case portion and including at least one UV-C LED configured to emit UV electromagnetic radiation, wherein the second case portion includes a mode button for activating a first sanitizing mode and a second sanitizing mode of the at least one UV-C LED. In the first sanitizing mode, the at least one UV-C LED is supplied with a first current, and in the second sanitizing mode the at least one UV-C LED is supplied with a second current which is greater than the first current and which overdrives the at least one UV-C LED to increase a radiant flux energy created for sanitizing the object.

BRIEF DESCRIPTION OF THE DRAWINGS

FIG. 10 is a schematic representation of exemplary UV-C LED placement and intensity in a UV sanitizing apparatus according to one or more embodiments;

FIG. 11 is an illustration of a single UV-C LED which may be utilized in a UV sanitizing apparatus according to one or more embodiments;

FIG. 12 is a perspective view of a UV sanitizing case in an expanded configuration according to one or more embodiments;

FIG. 22 is a block diagram illustrating the control electronics for a UV sanitizing apparatus according to one or more embodiments;

FIG. 23 is an end perspective view illustrating a safety feature of the UV sanitizing case according to one or more embodiments;

FIG. 24 illustrates a magnetic safety feature of the UV sanitizing case according to one or more embodiments;

FIG. 25 is a perspective view illustrating a charging port of the UV sanitizing case according to one or more embodiments;

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
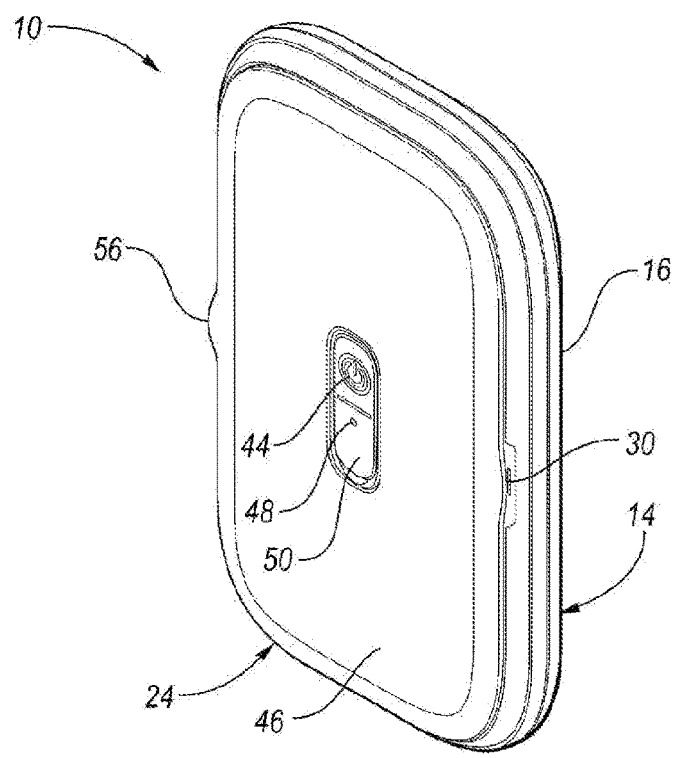
FIG. 1 is a perspective view of a UV sanitizing case in a collapsed configuration according to one or more embodiments.
Figure 2:
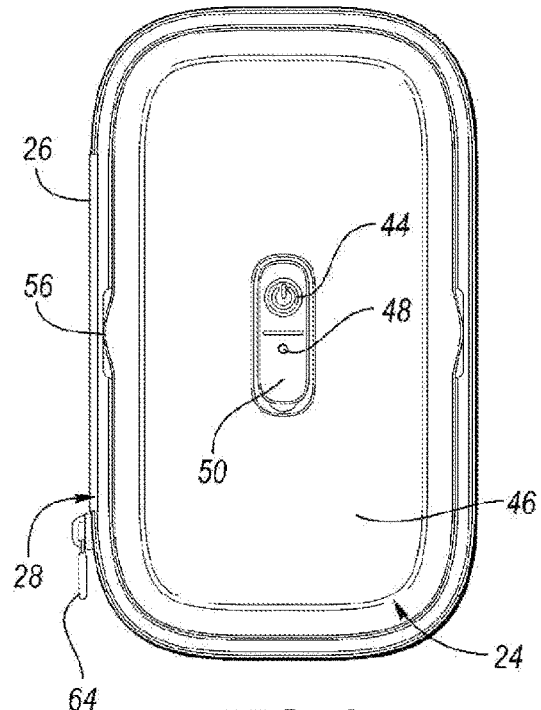
FIG. 2 is a front side view of the collapsed UV sanitizing case.
Figure 3:
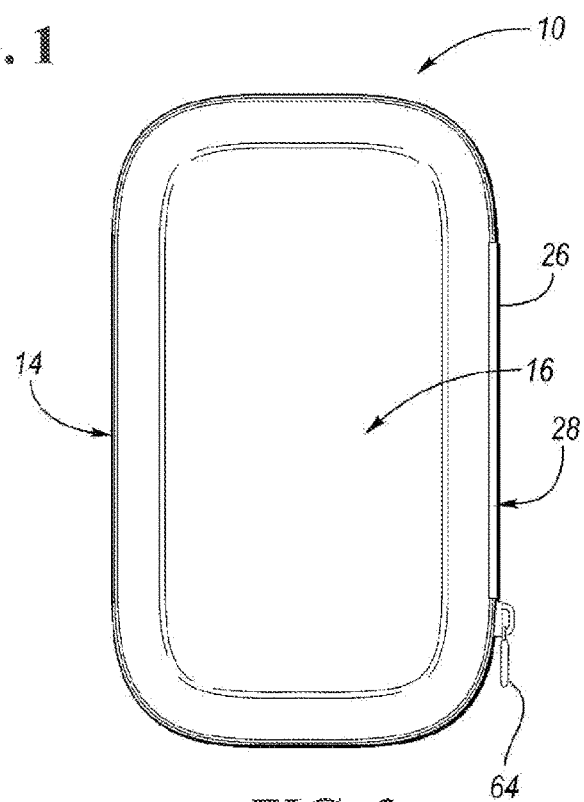
FIG. 3 is a rear side view of the collapsed UV sanitizing case.
Figure 4:
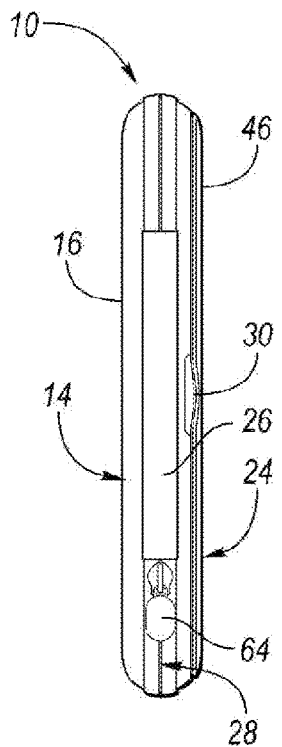
FIG. 4 is a left side view of the collapsed UV sanitizing case.
Figure 5:
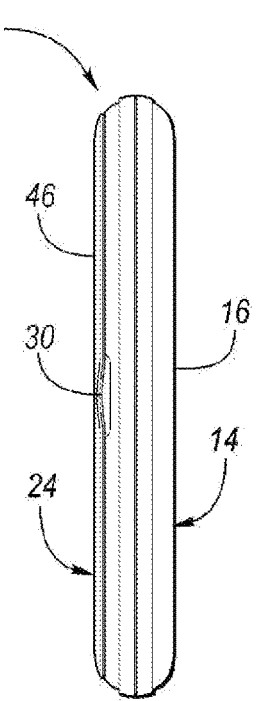
FIG. 5 is a right side view of the collapsed UV sanitizing case.
Figure 6:
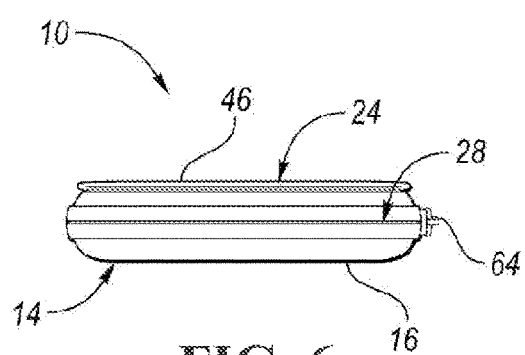
FIG. 6 is a top end view of the collapsed UV sanitizing case.
Figure 7:
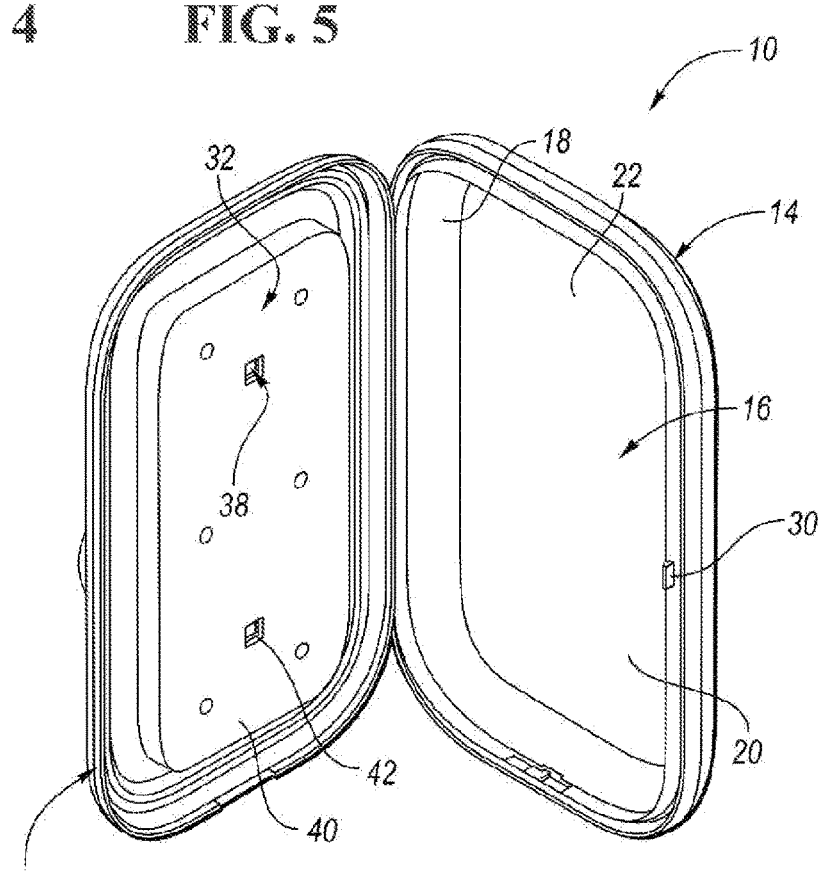
FIG. 7 is a perspective view of the collapsed UV sanitizing case in an open position.
Figure 8:
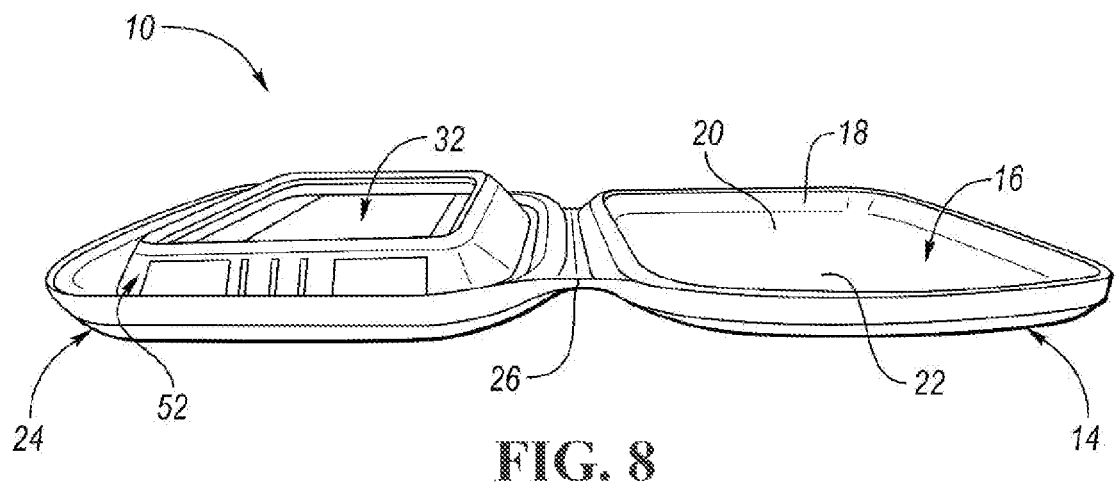
FIG. 8 is a side view of the collapsed UV sanitizing case in an open position.
Figure 9:
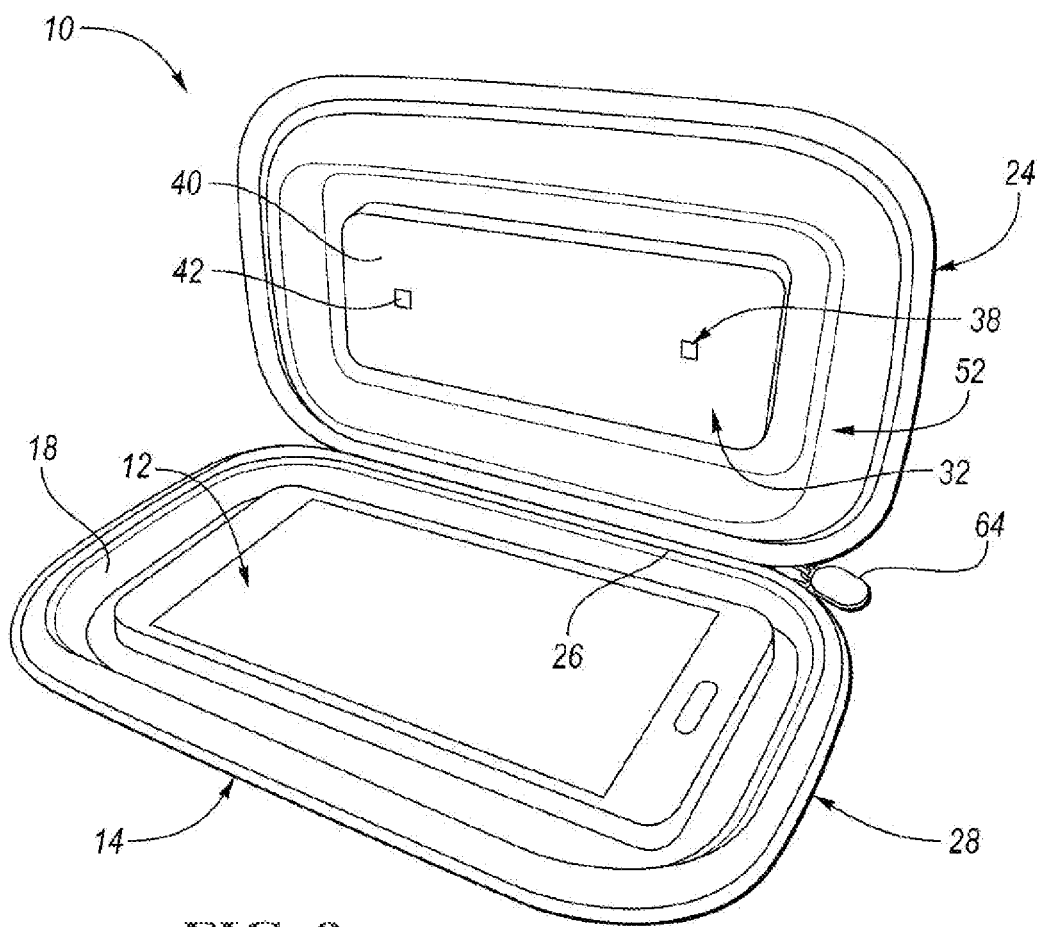
FIG. 9 is a perspective view of the collapsed UV sanitizing case in an open position with a mobile device received therein.

Disclosed herein are various embodiments of a portable sanitizing apparatus which uses ultraviolet (UV) light to sanitize objects and surfaces. With reference to FIGS. 1-9, a UV sanitizing case 10 is illustrated. In FIGS. 1-6, the case 10 is shown in a closed, collapsed position, whereas in FIGS. 7-9 the case 10 is depicted in an open, collapsed position. As illustrated, the case 10 may be generally rectangular in shape and may be sized to receive a mobile device 12, such as a smartphone (FIG. 9). In one or more embodiments, the case 10 is designed to fit all smartphones, regardless of size, make or model. In one non-limiting example, the case may be approximate 7-8 inches long and approximately 4-5 inches wide.

It is understood that different sizes and shapes of the case 10 may be provided to accommodate different types of mobile devices which, in addition to smartphones, may include tablets, computers, gaming devices, or other portable electronic devices. Still further, the case 10 could be configured to receive and sanitize devices other types of items such as, but not limited to, credit cards, glasses, watches, earphones, keys, wallet, utensils, pacifiers, baby toys, jewelry, hair accessories, combs, brushes, make-up accessories, pens, computer mouse, remote controls, and many other objects.

The case 10 may be constructed from plastic (e.g. polycarbonate (PC), thermoplastic polyurethane (TPU)), rubber, or metallic materials, and optionally may include a cloth or leather exterior cover. The plastic parts may include an antibacterial additive that helps with keeping the surfaces of the case 10 free of microbial activity. Plastics additives may include, but are not limited to, silver-based antimicrobial agents like AGION®, Microban antimicrobial plastic additives, and/or Biomaster TD100.

The case 10 includes a first case portion 14 arranged to receive an object to be sanitized, such as a mobile device 12. As best shown in FIGS. 7-8, the first case portion 14 includes a generally flat base 16 and optionally may include a sidewall structure 18 integrally formed with and extending upwardly from the base 16, defining a cavity 20. An inner surface 22 of the base 16 is arranged to removably receive the object to be sanitized. In one or more embodiments, the base inner surface 22 can be lined with an antimicrobial fabric. A second case portion 24 is connected to the first case portion 14, such as via a hinge 26. The first case portion 14 may be secured to the second case portion 24 via a zipper 28 around the perimeter of the case 10 or by an alternative mechanism, such as a latch 30.

The second case portion 24 includes a housing 32 with control electronics including a microcontroller unit (MCU) 34 (best shown in FIG. 22). A power source 36, such as a rechargeable lithium-ion battery, may also be mounted in the housing 32. Alternatively, the case 10 could operate as a plug-in device. The second case portion 24 further includes at least one light source 38, such as an LED, powered by the power source 36 and controlled by the MCU 34, wherein the light source 38 is configured to emit ultraviolet electromagnetic radiation for sanitizing contaminated surfaces. In one or more embodiments, the ultraviolet radiation is in the range of ultraviolet-C (UV-C) light. UV-C is a range of electromagnetic radiation having a wavelength ranging from approximately 100 nm to approximately 280 nm, where UV-C light has been demonstrated to be up to 99.9% effective in killing microorganisms including germs and bacteria. An inner wall 40 of the housing 32 includes a plurality of apertures 42 sized and aligned to correspond with the UV-C LEDs 38. Each aperture 42 includes transparent glass, plastic or other material to permit light from the LEDs 38 to pass through.

The case 10 further includes a power button 44 in electrical communication with the MCU 34 for activating the LEDs 38, and also optionally the intensity and duration of operation of the LEDs 38. The power button 44 may be located anywhere on the case 10, such as on the top surface 46 of the second case portion 24 as shown. The case 10 may further include an indicator light 48 for displaying the charging status of the battery 36 and the activation of the LEDs 38. In one non-limiting example, the indicator light 48 could be flashing blue when the LEDs 38 are operating and the sanitizing cycle is in progress, solid blue or turned off when the sanitizing cycle is complete, red when the battery 36 is low, flashing green when the battery 36 is charging, and solid green when the battery 36 is fully charged. Instead or in addition to the indicator light 48, the case 10 could include a progress indicator (not shown) such as a bar or dial to indicate cycle status, percent completion, and/or the state of charge of the battery 36.

Figure 13:
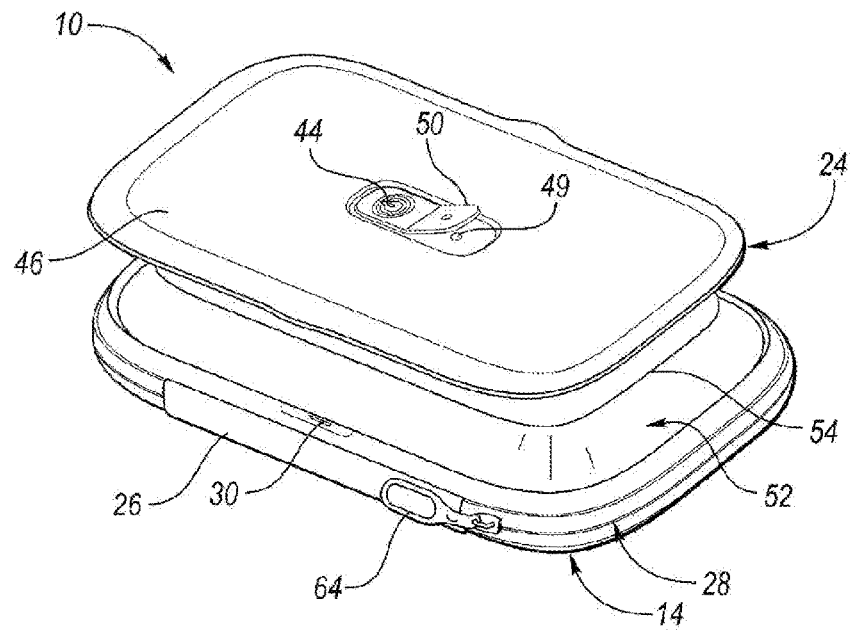
FIG. 13 is a side perspective view of the expanded UV sanitizing case.
Figures 14, 15, 16:
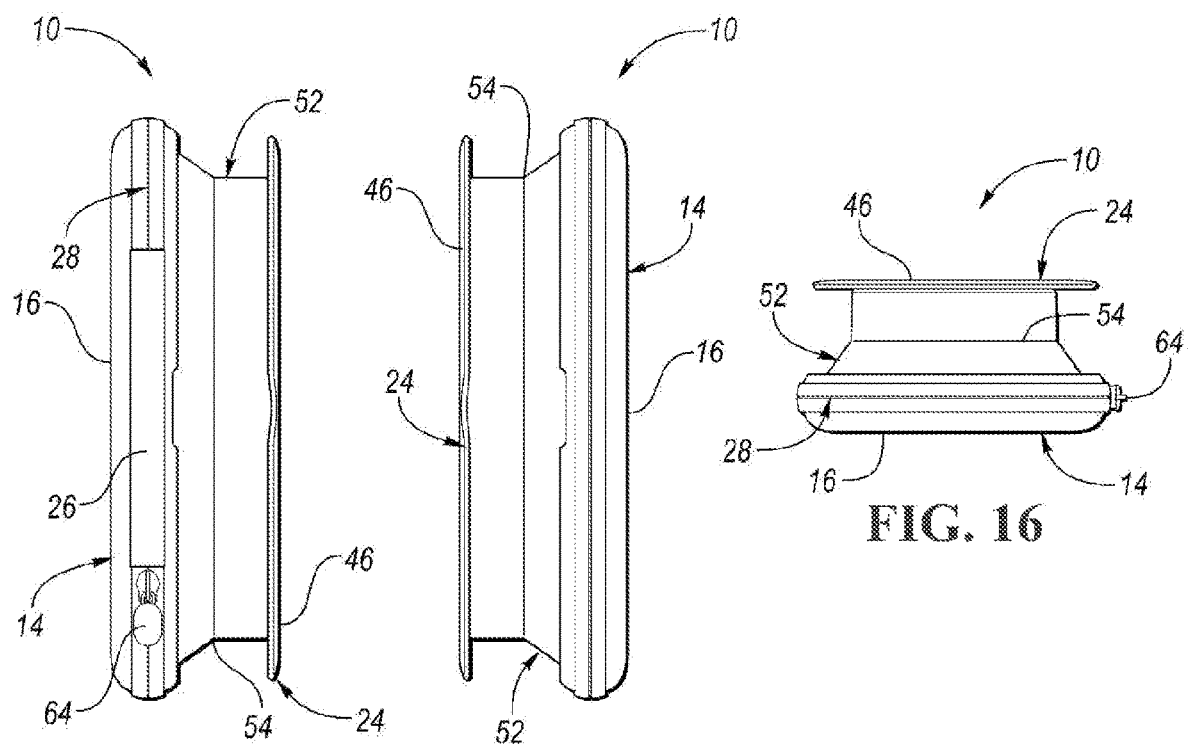
FIG. 14 is a left side view of the expanded UV sanitizing case.
FIG. 15 is a right side view of the expanded UV sanitizing case.
FIG. 16 is a top end view of the expanded UV sanitizing case.

The second case portion 24 includes a port 49 (FIGS. 13 and 25), such as under a flap 50 on the top surface 46, for receiving a connector of a charging cable for charging the battery 36. In one non-limiting example, it is contemplated that approximately 70 sanitizing cycles may be completed on a single charge of the battery 36. It is also contemplated that the case 10 could include a charging connector (not shown) within the first case portion 14 for charging a mobile device 12 from the battery 36 while in the case 10.

FIG. 10 is a schematic representation of exemplary LED 38 placement, coverage area, and intensity in the UV sanitizing case 10 according to one or more embodiments, and FIG. 11 is an illustration of a single LED 38 which may be utilized in the case 10. In the example shown, two LEDs 38 may be used and spaced 80 mm apart. Further LED specifications may include a radiant flux of 3.0 mW, a driving current of 20 mA, a forward voltage of 5.0 V, and a view angle 120 degrees, where each LED may have dimensions of 3.5 mm×3.5 mm×1.78 mm. Of course, these LED configurations and specifications are not intended to be limiting, and alternative LED configurations and specifications are also contemplated.

The LEDs 38 can have any shape and number and can be arranged in any manner to provide optimal coverage for sanitizing the target surface. For example, the LEDs 38 can be spaced linearly along the housing inner wall 40 of the second case portion 24 or in other patterns to provide the desired coverage for sanitizing. Instead of separate LEDs 38, the light source could include one or more elongated LED light pipes (not shown). Although LEDs 38 are shown herein in the second case portion 24, it is contemplated that LEDs 38 could also be provided in the first case portion 14. It is further contemplated that the angle of the LEDs 38 could be adjustable.

As indicated above, the power button 44 could also be used for mode selection between different sanitizing programs with different timing and different power/intensity settings. For example, a "standard" sanitizing mode may have the LEDs 38 supplied with a nominal current, for example, 100 mA. In a non-limiting example, the standard sanitizing mode may be activated with a short press of the power button 44 and may have a duration of approximately 30 seconds. Of course, it is understood that the sanitizing duration will be dependent on the number and placement of LEDs 38 or other light sources.

A "super" sanitizing mode may also be provided and may include overdriving the current to the UV LEDs 38. For example, the LEDs 38 may be supplied with a current of 120 mA (20% overdrive) to increase the radiant flux energy, and thereby increase antimicrobial efficacy and shorten cycle (treatment) time. In a non-limiting example, the super sanitizing mode may be activated with a long press of the power button 44 and may have a duration of approximately 60 seconds. Overdriving an LED can push the power to as much as 5× its rated power. In a non-limiting example, if the LEDs 38 are rated at 3 mW, they may be driven to 17.1 mW. That difference in radiant output results in a radiant flux of 5 over 30 seconds, whereas as much as 10 minutes would be needed to reach the same value if these LEDs were still at 3 mW. The intermittent use of an LED for a discrete timeframe enables it to be driven by a higher current than the "constant on" rating and deliver more power to the irradiate the target surface, where all the LEDs 38 do not have to be working at all times.

In order to kill bacteria and germs effectively, UV light must come into contact with the surface which is desired to be sanitized. In addition to light contact, the intensity of the UV light is important for the efficacy of the sanitization. When UV light reflects off any surface, it greatly diminishes the UV light intensity. Therefore, to have effective and efficient sanitization, the LED light needs to be directed at the target surface and be spaced from the target surface a sufficient distance to provide an optimal coverage area of the UV light. In one non-limiting example, this distance may be approximately 30 mm from the LEDs 38 to the surface of the mobile device. However, a case having LEDs fixed at this distance from the device surface would be less compact and portable than desired.

Accordingly, the UV sanitizing case 10 includes an expansion member 52 which can be expanded to increase the height of the second case portion 24 above the first case portion 14, and thus increase the distance from the LEDs 38 to the target surface to be sterilized, such as on a mobile device 12. The expansion member 52 may be incorporated in the second case portion 24, and allows the second case portion 24 to be positioned an optimal distance from the target surface when the LEDs 38 are activated while providing the ability to collapse and become compact for ease of portability and storage of the case 10 when sanitizing is completed.

Figure 17:
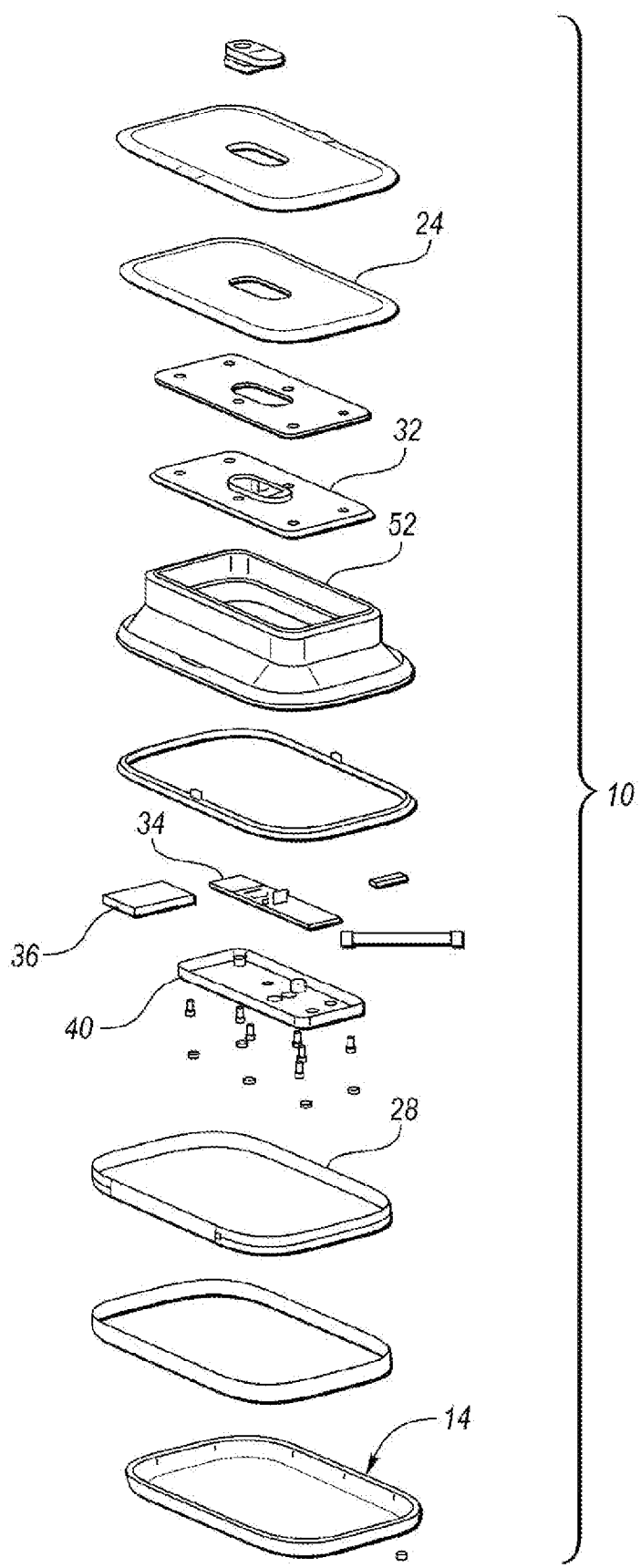
FIG. 17 is an exploded view of the UV sanitizing case according to one or more embodiments.

FIGS. 12-16 show the UV sanitizing case 10 in an expanded configuration, and FIG. 17 is an exploded view of the case 10 according to one or more embodiments. The expansion member 52 may be opaque to prevent light from being transmitted through the case 10 and may have at least one fold 54. The expansion member 52 may be constructed from any material with sufficient flexibility to fold into the collapsed position as well as rigidity to remain in the expanded position such as, but not limited to, thermoplastic TPU, TPE, rubber, or silicone. It is contemplated that the expansion member 52 could have varying height positions to provide different available distances from the LEDs 38 to the target surface. Tabs 56 may be provided on the second case portion 24 to facilitate gripping the second case portion 24 for expanding the expansion member 52. In one example, both sides of the case 10 do not have to expand equally.

Figure 18:
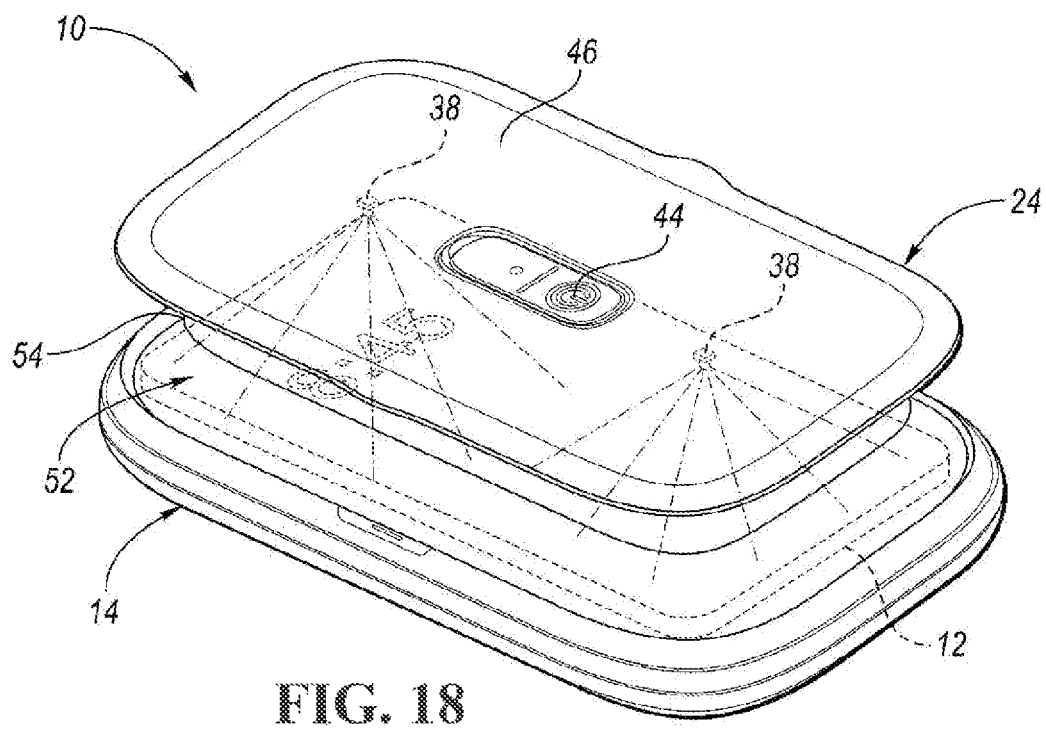
FIG. 18 is an illustration of an expanded UV sanitizing case in operation with a mobile device received therein according to one or more embodiments.

In operation, as illustrated in FIG. 18, a mobile device 12 or other object is inserted into the case 10, such as by unzipping the zipper 28 and placing the mobile device 12 in the first case portion 14. The case 10 may then be closed, such as by zipping the zipper 28. The expansion member 52 is expanded after or prior to insertion of the mobile device 12, such as by gripping the tabs 56 and pulling upward or outward. The user will depress the power button 44 to initiate the sanitizing cycle, activating the LEDs 38 and sanitizing the target surface. When the program is complete, the user can open (e.g. unzip) the case 10 and flip the mobile device 12 over to sanitize the opposite surface, can remove the mobile device 12 from the case 10 for use, or can store the mobile device in the case 10.

Figure 19:
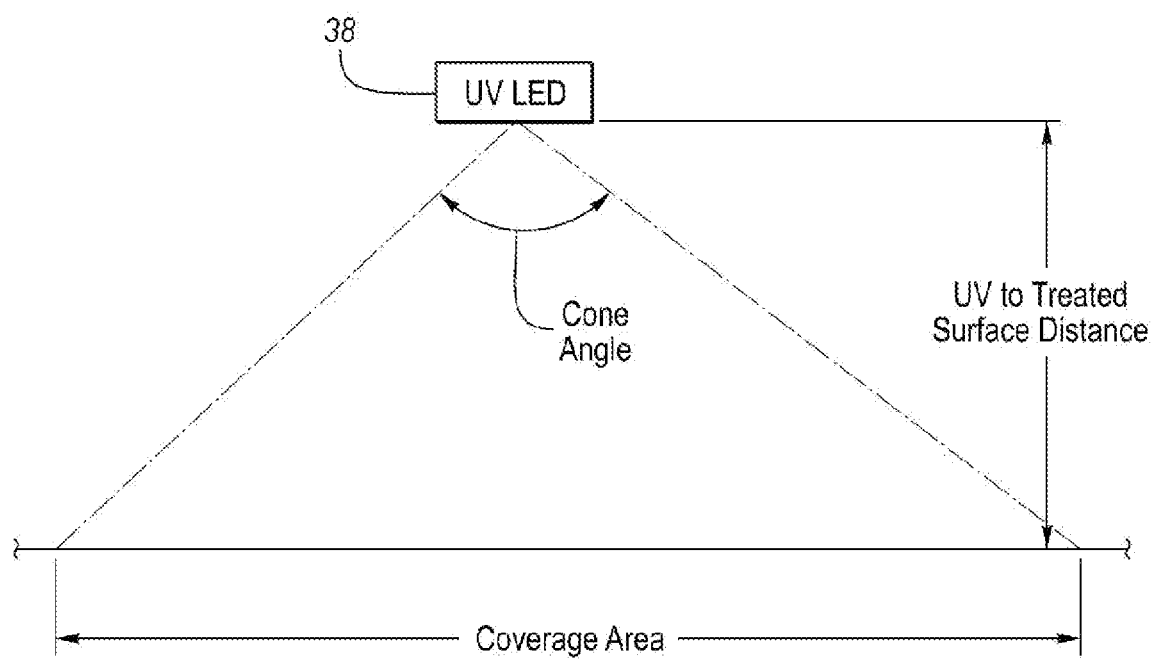
FIG. 19 is a schematic representation of an example light angle, distance to treated surface, and coverage area for a UV LED in a UV sanitizing apparatus according to one or more embodiments.

FIG. 19 is a schematic representation of an example cone angle, distance to treated surface, and coverage area for a UV LED in a UV sanitizing case 10 or other apparatus according to one or more embodiments. By using the expansion member 52 (pop-up mechanism) described above, embodiments disclosed herein are capable of having the UV LEDs 38 or other light source optimally positioned at a controlled distance from the target surface being treated and considering the angle of vision of the LEDs 38 to maximize the UV coverage area.

Figure 20:
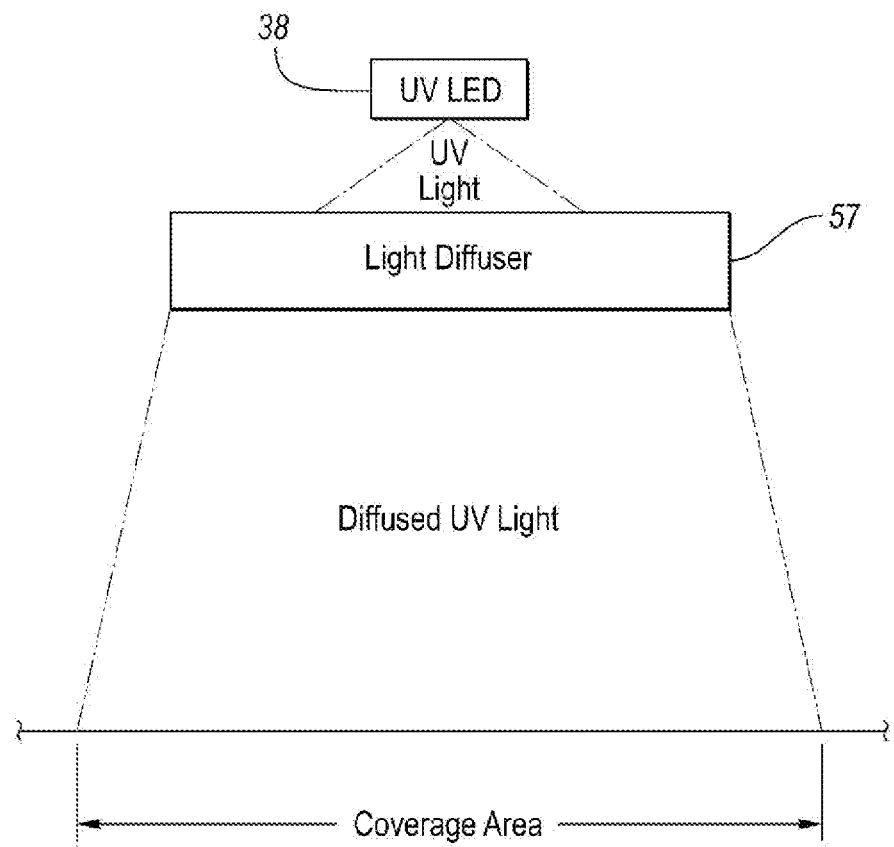
FIG. 20 is a schematic representation of an example coverage area for a UV LED with a light diffuser in a UV sanitizing apparatus according to one or more embodiments.

FIG. 20 is a schematic representation of an example coverage area for a UV LED 38 with a light diffuser 57 included in a UV sanitizing case 10 or apparatus, such as associated with the housing inner wall 40, according to one or more embodiments. Light diffusion removes the hot spot nature of an LED and instead spreads the light out evenly across an area. The light diffuser 57 may be constructed from any diffusion material which transfers the light energy as well as diffusing it such as, but not limited to, types of translucent polycarbonate with light diffusion additives added for UV diffusion (e.g. TUFFAK® DX-NR). In addition, the housing inner wall 40 or other parts of the first case portion 14 or second case portion 24 may include a reflective coating to reflect the UV-C rays and further increase coverage area, and may also be helpful for sanitizing objects with irregular shapes. Examples of possible reflective coatings are silver-based compounds, copper/nickel used as a middle layer and then coated with aluminum, and/or metallic materials, such as tantalum pentoxide (Ta2O5), aluminum oxide (Al2O3), or hafnium oxide (HfO2) that have high transmission in the LED emission spectrum.

Figure 21:
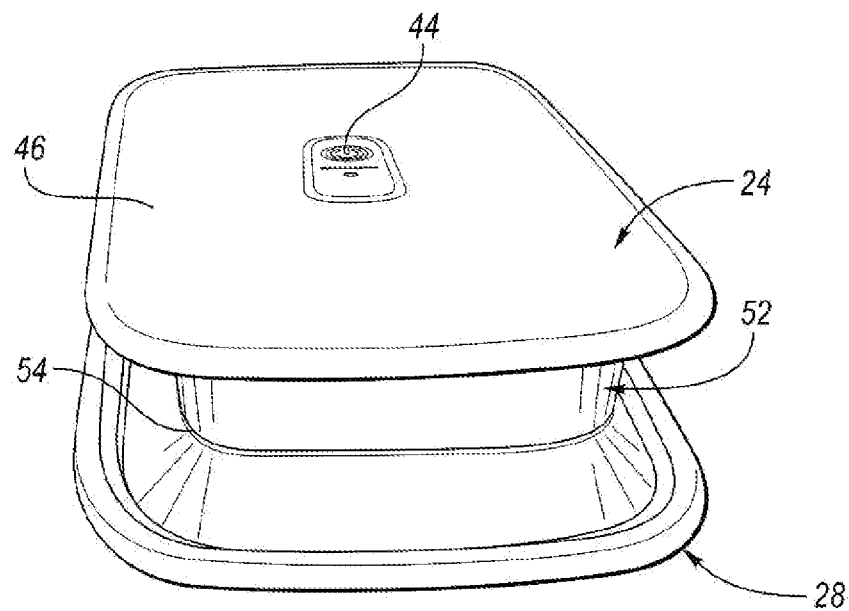
FIG. 21 is a perspective view of a UV sanitizing case with a first case portion detached according to one or more embodiments.

In one or more embodiments, the first case portion 14 and the second case portion 24 may be detachable from each other, where FIG. 21 illustrates the UV sanitizing case 10 with the first case portion 14 detached. In this way, the second case portion 24 can be used to sanitize a surface or object outside of the case 10. The second case portion 24 can be attachable to/detachable from the first case portion 14, for example, by a zipper 28, magnets, hook and loop material (e.g. VELCRO®), a snap-fit mechanism, a tongue and groove sliding mechanism, or other mechanisms.

The case 10 may be configured to automatically shut off the LEDs 38 if the MCU 34 detects that the case 10 is open. This safety feature avoids accidental illumination of UV light outside of the case 10, such as into a user's eyes. FIG. 23 illustrates one embodiment of such a safety feature of the UV sanitizing case 10, where the MCU 34 is in electrical communication via cables 58 with a sensor 60 disposed at the edge of the second case portion 24 to sense if the case 10 is opened. Examples of suitable sensors include, but are not limited to, a mechanical switch, a magnetic hall sensor 62 (FIG. 22), an infrared sensor, and a position sensor. As shown, the cables 58 may generally follow the contour of the expansion member 52, although the sensor 60 is not limited to the location shown.

FIG. 24 illustrates a magnetic safety feature of the UV sanitizing case 10 according to one or more embodiments. As shown, the zipper 28 includes a zipper pull member 64 with an integrated magnet (not shown), and a corresponding magnet 66 is disposed on the case 10, such as on the sidewall structure 18 or hinge 26 area, adjacent an end of the zipper 28. The magnet 66 is in communication with a magnetic hall sensor or switch 62 (FIG. 22) which, in turn, is in electrical communication with the MCU 34. In one or more embodiments, in order to execute the sanitizing cycle, the zipper 28 must be closed with the zipper pull member 64 positioned on the magnet 66 in an "on" position. If the zipper pull member 64 is not positioned as such, each prior to or during a sanitizing cycle, the hall sensor 62 is configured to communicate to the MCU 34 to prohibit or cease activation of the LEDs for the sanitizing cycle, acting as a safety lock. In this circumstance, the indicator light 48 may be used to indicate the error condition, such as by flashing red.

As another alternative safety feature, an accelerometer (not shown) may be provided to provide orientation information for the case 10 so that the LEDs 38 may be deactivated if the second case portion 24 is facing upwardly or at another specified angle. As yet another alternative, a proximity sensor (not shown) may be provided for detecting the distance to the surface to be disinfected, where the LEDs 38 may be turned off if the distance is beyond a predetermined threshold.

Figure 26:
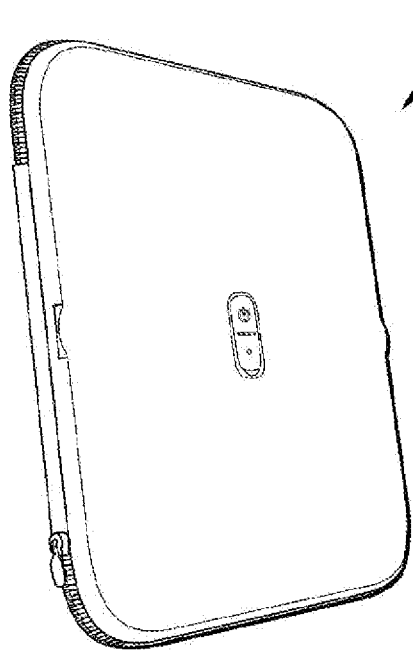
FIG. 26 is a perspective view of a larger UV sanitizing case, such as for a tablet, in a collapsed configuration according to one or more embodiments.
Figure 27:
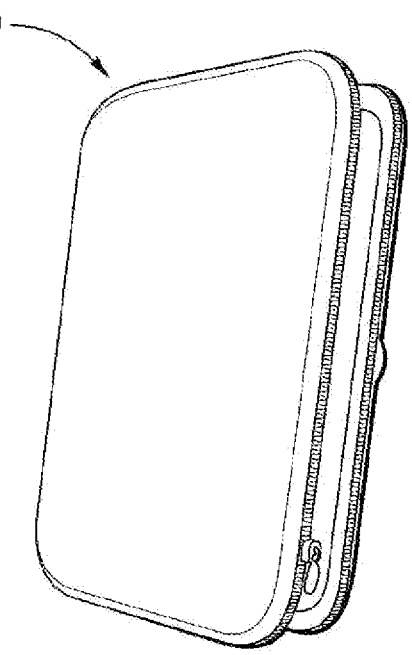
FIG. 27 is a perspective view of the UV sanitizing case of FIG. 26 in an expanded configuration.

FIG. 26 is a perspective view of a larger UV sanitizing case 110, such as for a tablet, in a collapsed configuration, and FIG. 27 illustrates this case 110 in an expanded configuration. The compact and collapsible design of the sanitizing case functions as a carrying case for travel with the ability to sanitize on-the-go. All of the description and features of the UV sanitizing case 10 explained above may be equally applicable to this larger case 110. Like features may be designated with like reference numerals with the addition of a "1" prefix.

Figure 28:
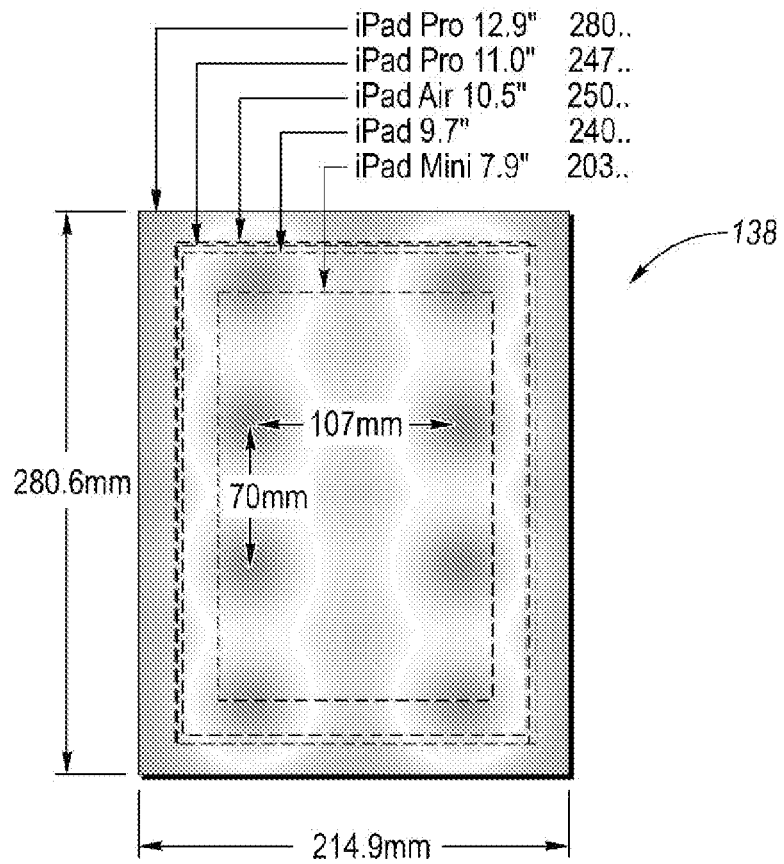
FIG. 28 is a schematic representation of exemplary UV-C LED placement and intensity in a UV sanitizing apparatus according to one or more embodiments.

FIG. 28 is a schematic representation of exemplary LED 138 placement, coverage area and intensity in the larger UV sanitizing case 110. As shown, eight LEDs 138 may be used in two linear arrays of four LEDs 138 each, with the LEDs 138 in each array spaced 70 mm apart and with the arrays spaced 107 mm from each other. Further LED specifications may include a radiant flux of 17.2 mW, a driving current of 115 mA, a forward voltage of 5.4 V, and a view angle 120 degrees. Of course, these LED configurations and specifications are not intended to be limiting, and alternative LED configurations and specifications are also contemplated.

Figure 29:
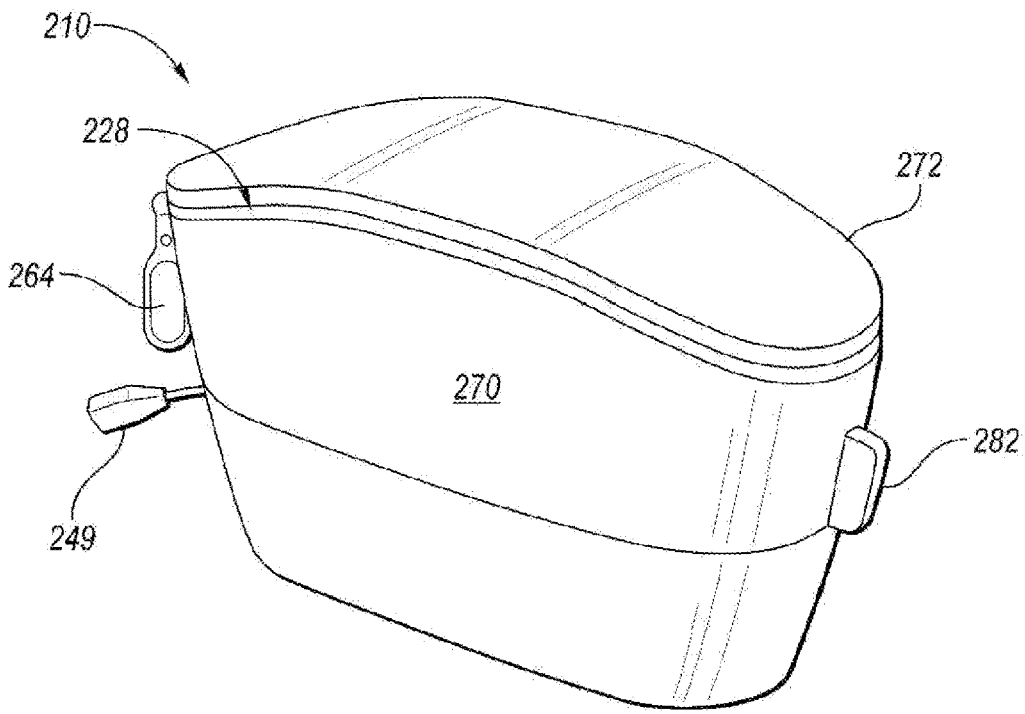
FIG. 29 is a perspective view of a UV sanitizing bag according to one or more embodiments.

FIG. 29 illustrates a UV sanitizing bag 210 which may sanitize mobile devices or other electronics or objects while being soft, portable and compact enough to easily fit in a purse or backpack. In one or more embodiments, the bag 210 may have a bottom panel 268, a sidewall structure 270 extending upwardly therefrom, and a top panel 272 which define an internal cavity 274 into which objects to be sanitized may be inserted. A zipper 228 is provided to secure the top panel 272 to the sidewall structure 270 In one non-limiting example, the bag 210 may be approximately 8 inches long and approximately 4 inches tall, although these dimensions and the aforementioned panel and sidewall structure are not intended to be limiting. Again, all of the description and features explained above with reference to the UV sanitizing cases 10, 110 may be equally applicable to the sanitizing bag 210. Like features may be designated with like reference numerals with the addition of a "2" prefix.

Figure 30:
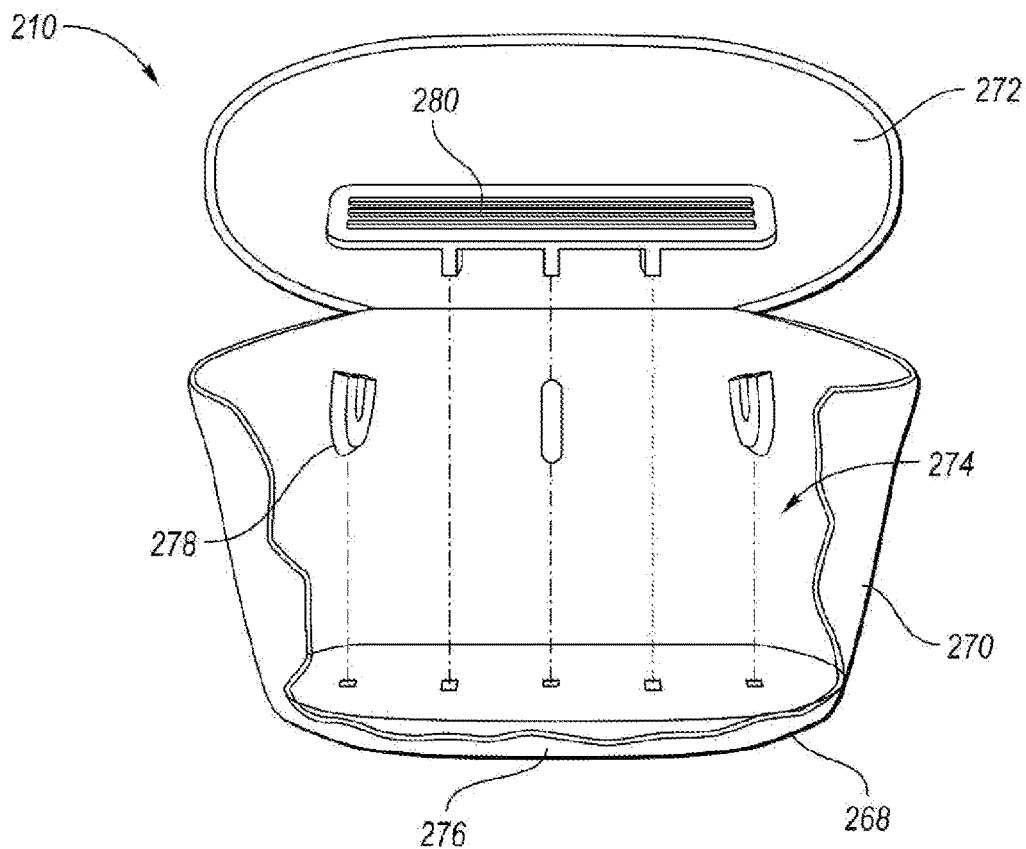
FIG. 30 is an illustration of interior components of the UV sanitizing bag including a base, clips, and platform according to one or more embodiments.
Figure 31:
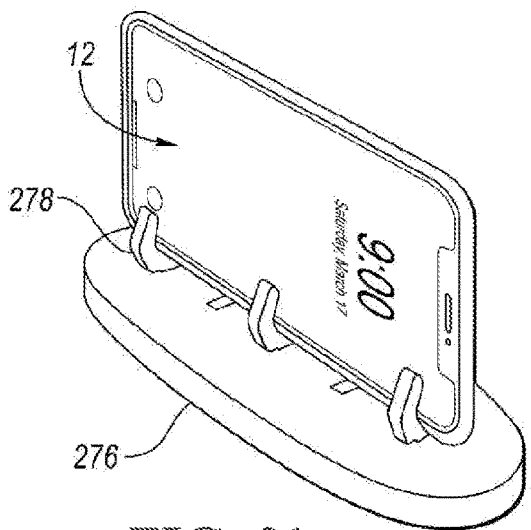
FIG. 31 is a perspective view of a mobile device held in position by clips received by the base.
Figure 32:
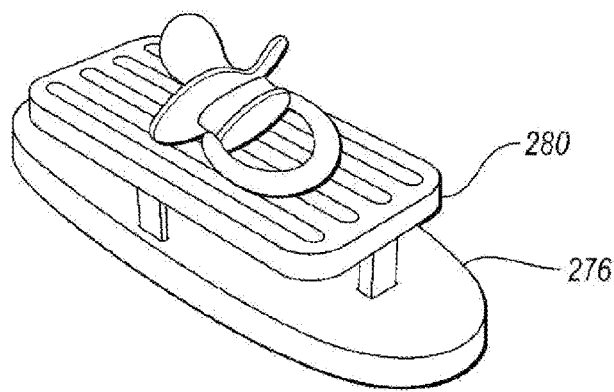
FIG. 32 is a perspective view of an exemplary object, a pacifier, positioned on the platform received by the base.

FIGS. 30-32 illustrate several interior components of the UV sanitizing bag 210 including a base 276, one or more clips 278, and a platform 280 which may each be constructed from a plastic material according to one or more embodiments. The base 276 may be removably or permanently affixed within the bag 210, such as along the bottom panel 268. Either the clips 278 or the platform 280 may be removably and interchangeably received by the base 276 and are arranged to hold items in position within the bag 210. Such components may be desirable to keep items in place and ensure optimal UV-C LED light exposure, maximizing effectiveness of the sanitizing cycle. FIG. 31 illustrates a mobile device 12 held in position by clips 278, and FIG. 32 illustrates an exemplary object, a pacifier, positioned on the platform 280.

Figure 33:
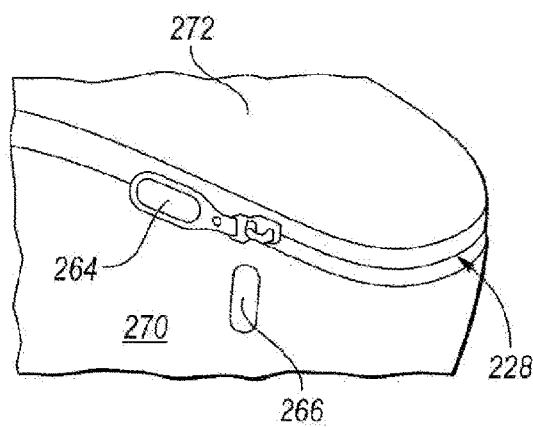
FIG. 33 is a perspective view of a magnetic safety feature of a UV sanitizing apparatus in an off position according to one or more embodiments.
Figure 34:
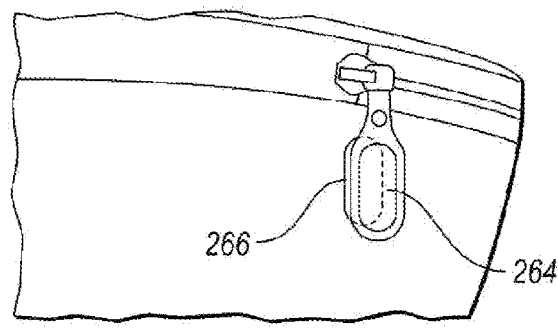
FIG. 34 is a side view of the magnetic safety feature of FIG. 33 in an on position.

As described above with reference to FIG. 24, FIGS. 33-34 illustrate a magnetic safety feature of the UV sanitizing bag 210 according to one or more embodiments. The zipper 228 includes a zipper pull member 264 with an integrated magnet (not shown), and a corresponding magnet 266 is disposed on the bag 210, such as on the sidewall structure 218 adjacent an end of the zipper 228. The magnet 266 is in communication with a magnetic hall sensor or switch 62 (FIG. 22) which, in turn, is in electrical communication with the MCU 34. In one or more embodiments, in order to execute the sanitizing cycle, the zipper 228 must be closed with the zipper pull member 264 positioned on the magnet 266 in an "on" position (FIG. 34). If the zipper pull member 264 is not positioned as such (FIG. 33), each prior to or during a sanitizing cycle, the hall sensor 62 is configured to communicate to the MCU 34 to prohibit or cease activation of the LEDs for the sanitizing cycle, acting as a safety lock.

Figure 35:
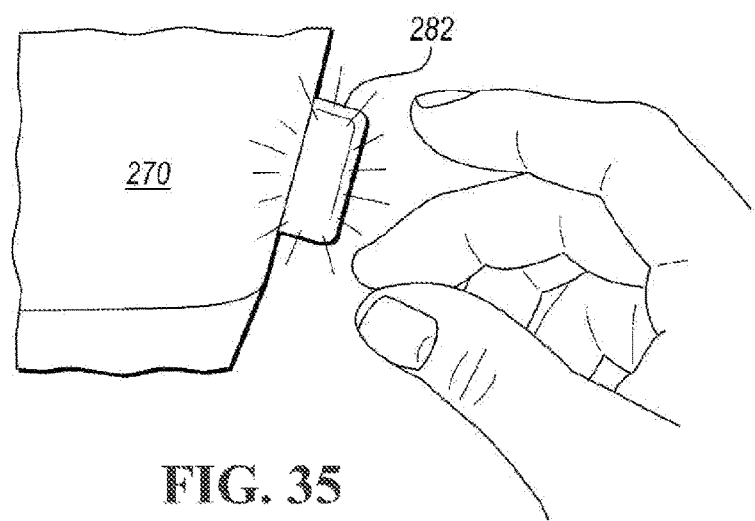
FIG. 35 is an illustration of a power button and indicator light for a UV sanitizing apparatus according to one or more embodiments.
Figure 36:
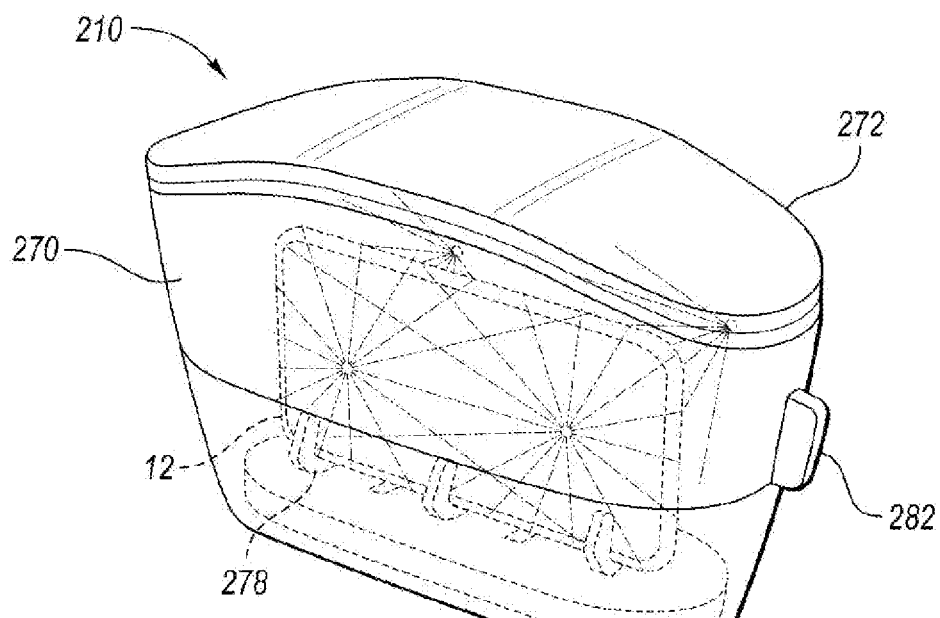
FIG. 36 is an illustration of a UV sanitizing bag in operation with a mobile device received therein according to one or more embodiments.

Referring to FIGS. 29 and 35, a flap 282 extending from the sidewall structure 218 may function as a combined power button, mode selector, and indicator light, although other locations of the flap 282 on the bag 210 are also contemplated. A charging port 249 may also extend from the sidewall structure 218 or another suitable location on the bag 210. In one non-limiting example, a single charge of the battery 36 may allow for approximately 18 sanitizing cycles. FIG. 36 is an illustration of the UV sanitizing bag 210 in operation with a mobile device 12 received therein according to one or more embodiments. In the example shown, four LEDs 238 may be used for sanitizing, two on each interior side of the bag 210, although other numbers and configurations of LEDs 238 are fully contemplated.

As described above with reference to FIG. 21, a UV sanitizing apparatus is contemplated which is not an enclosed case or bag. FIGS. 37-46 illustrate a UV sanitizing wand 310 which can be placed over any surface or object to sanitize it. The wand 310 is lightweight, portable and compact where, in one non-limiting example, the wand 310 may have dimensions of approximately 4-5 inches long and wide. All of the description and features provided above with reference to the UV sanitizing cases 10, 110 and the UV sanitizing bag 210 may be equally applicable to the sanitizing wand 310. Like features may be designated with like reference numerals with the addition of a "3" prefix.

Figure 37:
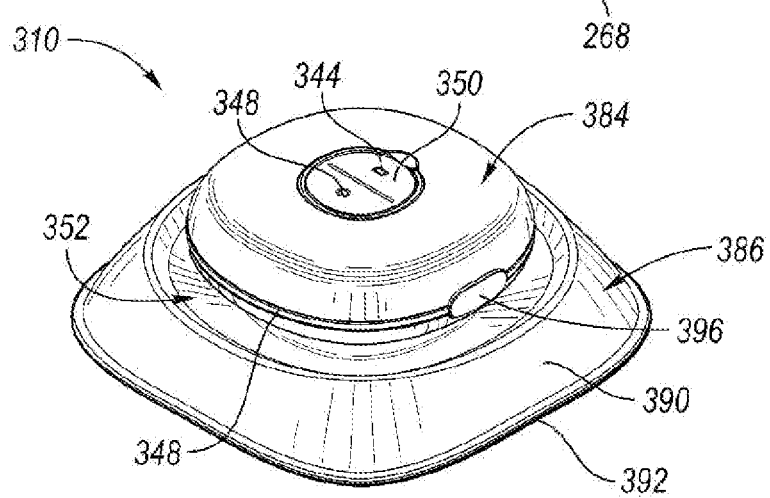
FIG. 37 is a perspective view of a UV sanitizing wand in a collapsed configuration according to one or more embodiments.
Figure 38:
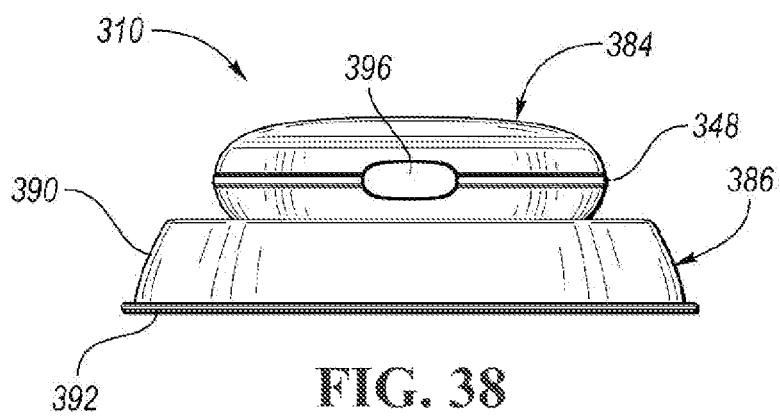
FIG. 38 is a side view of the collapsed UV sanitizing wand.
Figure 39:
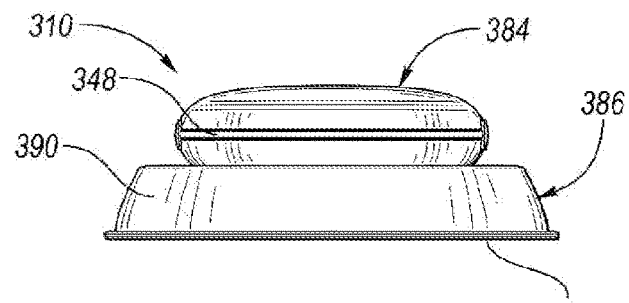
FIG. 39 is a front view of the collapsed UV sanitizing wand.
Figure 40:
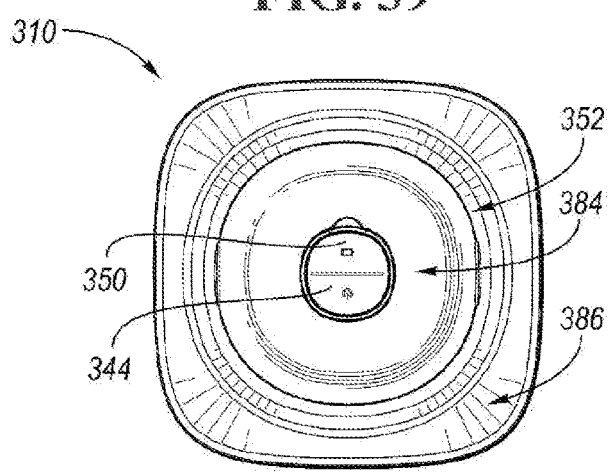
FIG. 40 is a top view of a UV sanitizing wand according to one or more embodiments.
Figure 41:
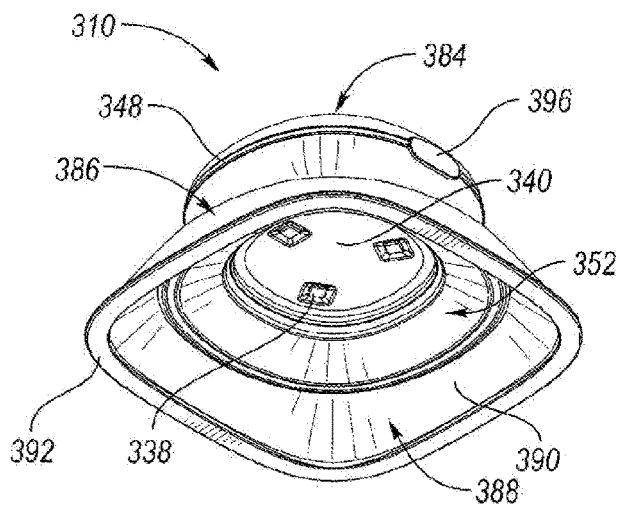
FIG. 41 is a bottom perspective view of a UV sanitizing wand according to one or more embodiments.
Figure 42:
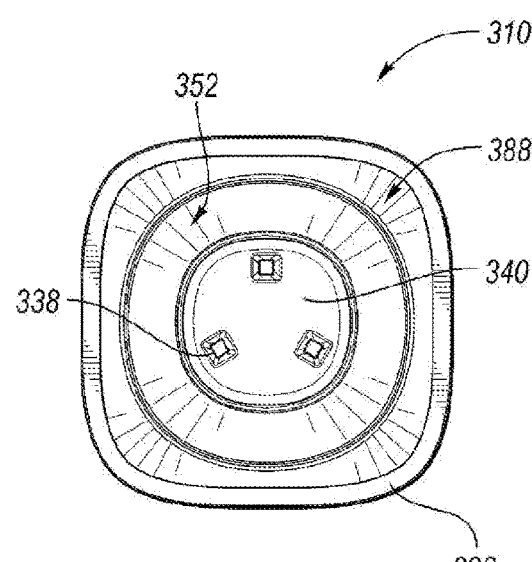
FIG. 42 is a bottom view of a UV sanitizing wand according to one or more embodiments.
Figure 43:
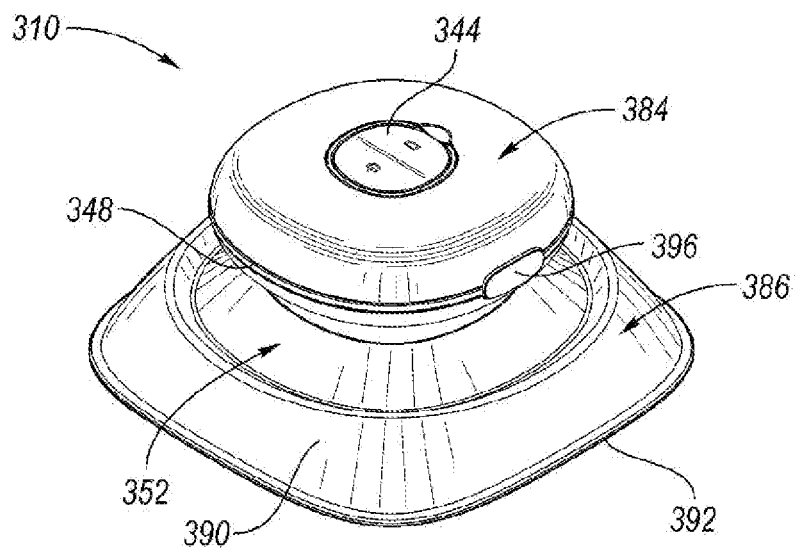
FIG. 43 is a perspective view of a UV sanitizing wand in an expanded configuration according to one or more embodiments.
Figure 44:
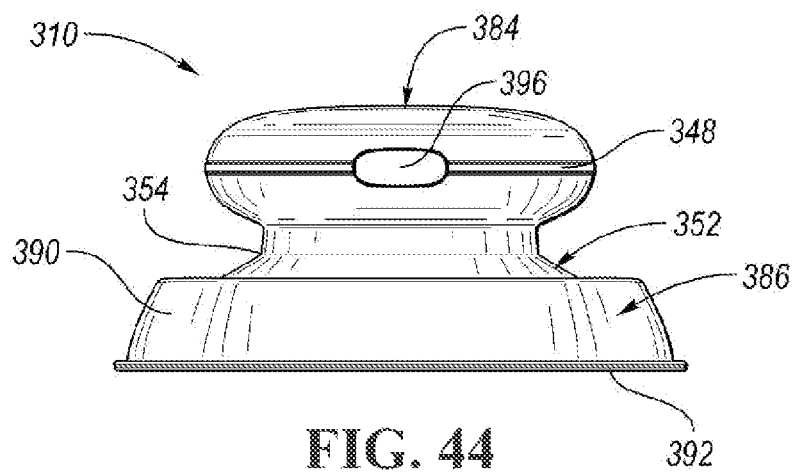
FIG. 44 is a side view of the expanded UV sanitizing wand.
Figure 45:
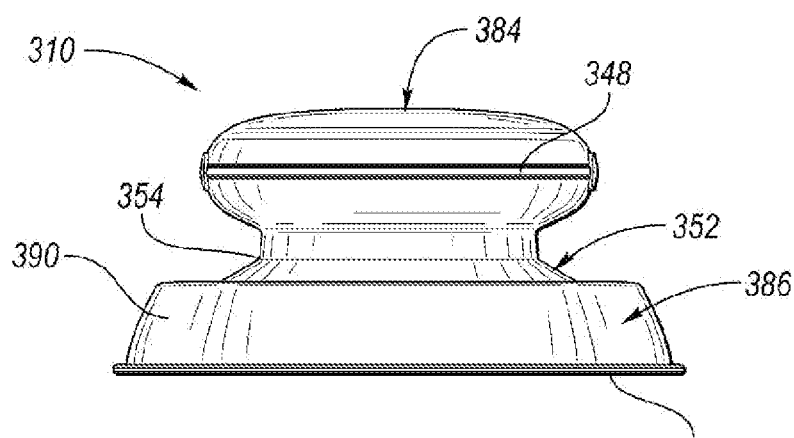
FIG. 45 is a front view of the expanded UV sanitizing wand.
Figure 46:
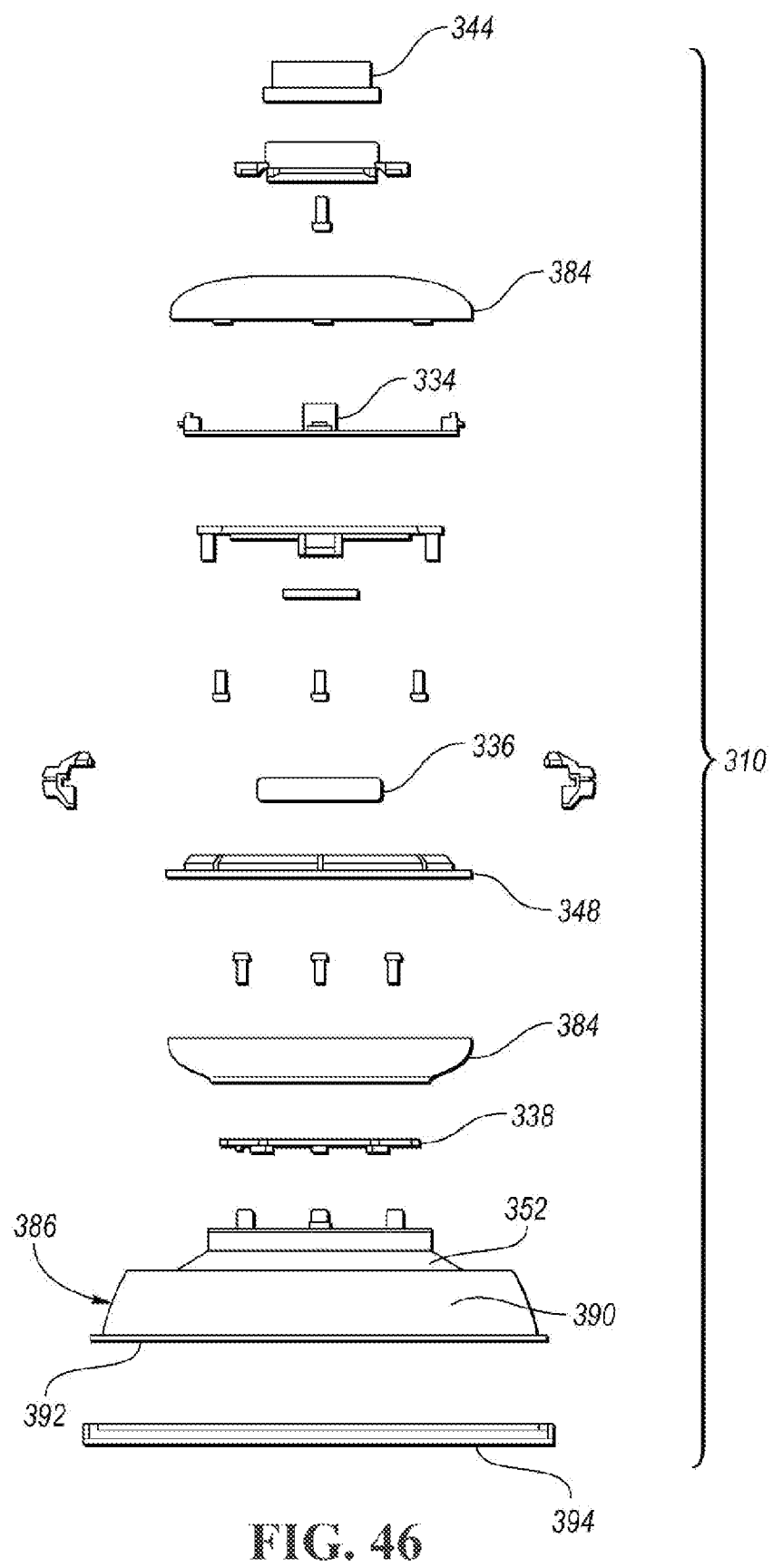
FIG. 46 is an exploded view of a UV sanitizing wand according to one or more embodiments.

In FIGS. 37-39, the wand 310 is shown in a collapsed configuration, and in FIGS. 43-45 the wand 310 is shown in an expanded configuration. The wand 310 includes top housing portion 384, a base portion 386, and an expansion member 352 connected therebetween, wherein an inner surface of the expansion member 352 and the base portion 386 define a cavity 388 arranged to removably cover an object or surface to be sanitized. In one or more embodiments, the base portion 386 may include a wall structure 390 with a bottom rim 392. In one non-limiting example, the bottom rim 392 may have a width of approximately 5 mm. The bottom rim 392 is arranged to contact a surface, either on which an object to be sanitized is placed or a surface which itself is to be sanitized. The bottom rim 392 may provide a seal against the surface, prohibiting UV light from escaping from the wand 310, providing safety, efficacy, and reliable positioning.

The top housing portion 384 may serve as a grip for the user and houses the control electronics and power source (e.g. MCU 34 and battery 36), such as described above with reference to FIG. 22. The top housing portion 384 further includes at least one light source 338, such as an LED, powered by the power source 36 and controlled by the MCU 34, wherein the light source 338 is configured to emit ultraviolet electromagnetic radiation for sanitizing contaminated surfaces. An inner wall 340 of the top housing portion 384 includes a plurality of apertures 342 sized and aligned to correspond with the UV-C LEDs 338. While three LEDs 338 are depicted herein, it is understood that the LEDs 338 can have any shape and number and can be arranged in any manner to provide optimal coverage for sanitizing the target surface.

The top housing portion 384 further includes a power button 344 in electrical communication with the MCU 34 for activating the LEDs 338, and also optionally the intensity and duration of operation of the LEDs 338. The wand 310 may further include an indicator light 348 for displaying the charging status of the battery 336 and the activation of the LEDs 338. The top housing portion 384 includes a port 349, such as under a flap 350 on the top surface 46, for receiving a connector of a charging cable for charging the battery 336. A bottom cover 394 can be provided which is arranged to fit over the bottom rim 392 when the wand 310 is not in use (see FIG. 46).

The expansion member 352 can be expanded to increase the height of the top housing portion 384, or the distance between the top housing portion 384 and the base portion 386, and thus increase the distance from the LEDs 338 to the target surface to be sterilized. The expansion member 352 allows inner wall 340 to be positioned an optimal distance from the target surface when the LEDs 338 are activated while providing the ability to collapse and become compact for ease of portability and storage of the wand 310 when sanitizing is completed.

To sanitize a surface or object, the expansion member 352 is expanded, such as by gripping the top housing portion 384 and pulling upward or outward. Next, the power button 344 is depressed to initiate the sanitizing cycle. However, to ensure safe operation of the wand 310, an additional step may be required in order to activate the LEDs 338. In one or more embodiments, side buttons 396 may be provided on the top housing portion 384 or another suitable location on the wand 310. The side buttons 396 may be in electrical communication with a magnetic hall sensor or switch 62 (FIG. 22) which, in turn, is in electrical communication with the MCU 34 as described for previous embodiments. According to one or more embodiments, after depressing the power button (such as, but not limited to, within approximately 10 seconds), the LEDs 338 will be activated only if both side buttons 396 are pressed and held. If one or both of the side buttons 396 are released, the hall sensor 62 is configured to communicate to the MCU 34 to prohibit or cease activation of the LEDs 338 for the sanitizing cycle, acting as a safety lock. Once the LEDs 338 are activated, the wand 310 may be placed over any surface or object for sanitizing.

In this and other embodiments described above, the pop-up capability provided by the expansion member allows the UV sanitizing apparatus to expand and collapse in order to maximize UV light coverage and efficacy during sanitization while offering a compact portable form when not in use. It is understood that any UV sanitizing apparatus which utilizes an adjustable and/or collapsible and expandable elevation of the light source is fully contemplated, and is not limited to the shape, size, configuration, or form factors disclosed herein.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A portable sanitizing wand, comprising:
   a top housing portion including at least one UV light source configured to emit UV electromagnetic radiation;
   a base portion arranged to be placed over a surface or object to be sanitized, wherein the base portion includes a wall structure with a bottom rim extending generally horizontally with respect to the wall structure; and
   an expansion member connected between the top housing portion and the base portion, the expansion member having a collapsed configuration and an expanded configuration,
   wherein when the expansion member is in the expanded configuration, a distance between the top housing portion and the base portion is increased compared to when the expansion member is in the collapsed configuration, thereby increasing a distance from the at least one UV light source to the surface or object to be sanitized.

2. The portable sanitizing wand of claim 1, wherein the top housing portion includes an inner wall in which the at least one UV light source is disposed, and the inner wall, the expansion member and the base portion define a cavity and are arranged to removably cover the surface or object to be sanitized.

3. The portable sanitizing wand of claim 1, wherein the top housing portion includes a microcontroller unit and a battery disposed therein.

4. The portable sanitizing wand of claim 3, wherein the at least one UV light source includes a UV-C LED powered by the battery and controlled by the microcontroller unit.

5. The portable sanitizing wand of claim 3, wherein the top housing portion includes a power button in electrical communication with the microcontroller unit for activating the at least one UV light source.

6. The portable sanitizing wand of claim 3, further comprising side buttons provided on the top housing portion in electrical communication with the microcontroller unit for controlling activation of the at least one UV light source.

7. The portable sanitizing wand of claim 6, wherein continued depression of the side buttons is required in order to maintain activation of the at least one UV light source.

8. The portable sanitizing wand of claim 1, further comprising a bottom cover arranged to fit over the bottom rim.

9. A portable sanitizing wand, comprising:
   a top housing portion including at least one UV light source configured to emit UV electromagnetic radiation, the top housing portion including a microcontroller unit and a battery disposed therein, the top housing portion including side buttons in electrical communication with the microcontroller unit for controlling activation of the at least one UV light source;
   a base portion arranged to be placed over a surface or object to be sanitized; and
   an expansion member connected between the top housing portion and the base portion, the expansion member having a collapsed configuration and an expanded configuration,
   wherein when the expansion member is in the expanded configuration, a distance between the top housing portion and the base portion is increased compared to when the expansion member is in the collapsed configuration, thereby increasing a distance from the at least one UV light source to the surface or object to be sanitized.

10. The portable sanitizing wand of claim 9, wherein the top housing portion includes an inner wall in which at least one UV light source is disposed, and the inner wall, the expansion member and the base portion define a cavity and are arranged to removably cover the surface or object to be sanitized.

11. The portable sanitizing wand of claim 9, wherein the at least one UV light source includes a UV-C LED powered by the battery and controlled by the microcontroller unit.

12. The portable sanitizing wand of claim 9, wherein the top housing portion includes a power button in electrical communication with the microcontroller unit for activating the at leas tone UV light source.

13. The portable sanitizing wand of claim 9, wherein continued depression of the side buttons is required in order to maintain activation of the at least one UV light source.

14. The portable sanitizing wand of claim 9, wherein the base portion includes a wall structure with a bottom rim, and the portable sanitizing wand further comprises a bottom cover arranged to fit over the bottom rim.

15. A portable sanitizing wand, comprising:
   a top housing portion including at least one UV light source configured to emit UV electromagnetic radiation;
   a base portion arranged to be placed over a surface or object to be sanitized, the base portion including a bottom rim;
   a bottom cover arranged to fit over the bottom rim; and
   an expansion member connected between the top housing portion and the base portion, the expansion member having a collapsed configuration and an expanded configuration,
   wherein when the expansion member is in the expanded configuration, a distance between the top housing portion and the base portion is increased compared to when the expansion member is in the collapsed configuration, thereby increasing a distance from the at least one UV light source to the surface or object to be sanitized.

16. The portable sanitizing wand of claim 15, wherein the top housing portion includes an inner wall in which the at least one UV light source is disposed, and the inner wall, the expansion member and the base portion define a cavity and are arranged to removably cover the surface or object to be sanitized.

17. The portable sanitizing wand of claim 15, wherein the top housing portion includes a microcontroller unit and a battery disposed therein.

18. The portable sanitizing wand of claim 17, wherein the at least one UV light source includes a UV-C LED powered by the battery and controlled by the microcontroller unit.

19. The portable sanitizing wand of claim 17, wherein the top housing portion includes a power button in electrical communication with the microcontroller unit for activating the at least one UV light source.

20. The portable sanitizing wand of claim 17, further comprising side buttons provided on the top housing portion in electrical communication with the microcontroller unit for controlling activation of the at least one UV light source.

21. The portable sanitizing wand of claim 20, wherein continued depression of the side buttons is required in order to maintain activation of the at least one UV light source.

\* \* \* \* \*

UNITED STATES PATENT AND TRADEMARK OFFICE
CERTIFICATE OF CORRECTION

| | | |
|---|---|---|
| PATENT NO. | : 12,070,527 B2 | Page 1 of 1 |
| APPLICATION NO. | : 18/366045 | |
| DATED | : August 27, 2024 | |
| INVENTOR(S) | : David Yang et al. | |

It is certified that error appears in the above-identified patent and that said Letters Patent is hereby corrected as shown below:

In the Claims

Column 12, Line 38, Claim 12:
After "microcontroller unit for activating the at"
Delete "leas tone" and
Insert -- least one --.

Signed and Sealed this
Twenty-seventh Day of May, 2025

Coke Morgan Stewart
*Acting Director of the United States Patent and Trademark Office*